United States Patent [19]

Ueda et al.

[11] Patent Number: 4,855,292

[45] Date of Patent: Aug. 8, 1989

[54] 1-CYCLOPROPYL-6-FLUORO-8-ALKYL-1,4-DIHYDRO-4-OXO-QUINOLINE-3-CARBOXYLIC ACID DERIVATIVES

[75] Inventors: Hiraki Ueda; Hisashi Miyamoto; Shinji Aki; Tatsuya Otsuka, all of Tokushima, Japan

[73] Assignee: Otsuka Pharmaceutical Company, Limited, Japan

[21] Appl. No.: 76,888

[22] Filed: Jul. 23, 1987

Related U.S. Application Data

[63] Continuation-in-part of Ser. No. 17,247, Feb. 20, 1987, abandoned.

[30] Foreign Application Priority Data

| Feb. 25, 1986 | [JP] | Japan | 61-40921 |
| May 8, 1986 | [JP] | Japan | 61-105655 |
| May 22, 1986 | [JP] | Japan | 61-118568 |
| Jul. 23, 1986 | [JP] | Japan | 61-173370 |
| Aug. 19, 1986 | [JP] | Japan | 61-193838 |
| Sep. 30, 1986 | [JP] | Japan | 61-233837 |
| Oct. 15, 1986 | [JP] | Japan | 61-246050 |
| Dec. 18, 1986 | [JP] | Japan | 61-303515 |
| Feb. 19, 1987 | [JP] | Japan | 62-37000 |

[51] Int. Cl.$^4$ ............... A61K 31/47; C07D 401/04
[52] U.S. Cl. ............... 514/312; 546/156; 544/363; 544/389; 544/395; 548/557; 548/567; 548/568; 558/54; 558/388; 558/418; 558/425; 560/53; 560/51; 560/103; 562/493; 562/494; 564/215; 564/440; 564/441; 564/442; 260/544 R; 568/812; 568/938; 568/709; 570/182
[58] Field of Search ............... 514/312; 546/156

[56] References Cited

U.S. PATENT DOCUMENTS

| 4,544,747 | 10/1985 | Ishikawa et al. | 546/156 |
| 4,556,658 | 12/1985 | Grohe et al. | 514/254 |
| 4,563,459 | 1/1986 | Grohe et al. | 514/254 |
| 4,578,473 | 3/1986 | Domagala et al. | 546/156 |
| 4,705,788 | 11/1987 | Schriewer et al. | 546/156 |
| 4,753,953 | 6/1988 | Masuzawa et al. | 514/312 |

FOREIGN PATENT DOCUMENTS

| 0153163 | 2/1985 | European Pat. Off. . |
| 0153828 | 2/1985 | European Pat. Off. . |
| 0195841 | 5/1985 | European Pat. Off. . |
| 0172651 | 7/1985 | European Pat. Off. . |
| 0183129 | 11/1985 | European Pat. Off. . |
| 0191451 | 2/1986 | European Pat. Off. . |
| 0198192 | 3/1986 | European Pat. Off. . |
| 0202763 | 4/1986 | European Pat. Off. . |
| 208210 | 1/1987 | European Pat. Off. . |
| 3608745 | 1/1987 | Fed. Rep. of Germany . |
| 166681 | 8/1985 | Japan . |
| 126082 | 6/1986 | Japan . |
| 229877 | 10/1986 | Japan . |
| 81/6080 | 9/1981 | South Africa . |
| 85/4792 | 6/1985 | South Africa . |
| 1502405 | 6/1976 | United Kingdom . |
| 2057440 | 8/1980 | United Kingdom . |
| 86/06630 | 11/1986 | World Int. Prop. O. . |

OTHER PUBLICATIONS

Masuzawa et al., Chemical Abstracts, vol. 108, No. 75 234m (1988).
Research Disclosure 269024 "Use of Gyrase Inhibitors in Aerosol Form for Treating Respiratory Infections", (Sep. 1986).
Research Disclosure 269008 "Use of Gyrase Inhibitors for Treating Infections by Rectal or Vaginal Administration", (Sep. 1986).
Derwent Abstract No. 86-309519/47 for Japan Patent 229877 (10/14/86).
Derwent Abstract No. 86-193394/30 for Japan Patent 1126-082 (6/13/86).
Derwent Abstract No. 85-305531/49 for Japan Patent 166681 (8/29/85).

Primary Examiner—Anton H. Sutto
Assistant Examiner—E. Bernhardt
Attorney, Agent, or Firm—Wegner & Bretschneider

[57] ABSTRACT

Novel 4-oxoquinoline-3-carboxylic acid compounds of the formula:

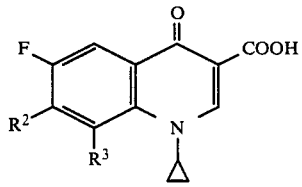

[1]

wherein $R^2$ is 1-pyrrolidinyl which may have 1 to 3 substituents selected from the group consisting of (i) $C_1$–$C_6$ alkyl, (ii) amino-($C_1$–$C_6$)alkyl, said amino being optionally substituted by 1 or 2 substituents selected from $C_1$–$C_6$ alkyl, $C_1$–$C_6$ alkanoyl, and $C_1$–$C_6$ alkoxycarbonyl, (iii) amino which may be substituted by 1 or 2 substituents selected from $C_1$–$C_6$ alkyl, phenyl($C_1$–$C_6$)alkyl, $C_1$–$C_6$ alkoxycarbonyl, and $C_1$–$C_6$ alkanoyl, and (iv) 2-oxo-1,3-dioxolenemethylamino which is substituted by $C_1$–$C_6$ alkyl; or 1-piperidinyl which may have 1 to 3 substituents selected from oxo, hydroxy, halogen and $C_1$–$C_6$ alkyl, and $R^3$ is $C_1$–$C_6$ alkyl, or a pharmaceutically acceptable salt thereof, said compounds having excellent antimicrobial activity and hence being useful as an antimicrobial agent, and a pharmaceutical composition containing said compound as an active ingredient.

30 Claims, No Drawings

1-CYCLOPROPYL-6-FLUORO-8-ALKYL-1,4-DIHYDRO-4-OXO-QUINOLINE-3-CARBOXYLIC ACID DERIVATIVES

This is a Continuation-in-part application of U.S. Ser. No. 017,247 filed on Feb. 20, 1987, now abandoned.

The present invention relates to novel antimicrobial benzoheterocyclic compounds of the formula [I]:

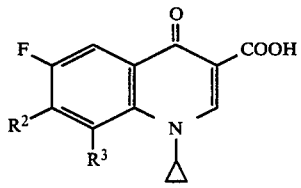

wherein $R^2$ is 1-pyrrolidinyl group which may have 1 to 3 substituents selected from the group consisting of (i) a $C_1$-$C_6$ alkyl group, (ii) an amino-($C_1$-$C_6$)alkyl group, said amino group being optinally substituted by 1 to 2 substituents selected from the group consisting of a $C_1$-$C_6$ alkyl group, a $C_1$-$C_6$ alkanoyl group, and a $C_1$-$C_6$ alkoxycarbonyl group, (iii) an amino group which may be substituted by 1 or 2 substituents selected from the group consisting of a $C_1$-$C_6$ alkyl group, a phenyl($C_1$-$C_6$)alkyl group, a $C_1$-$C_6$ alkoxycarbonyl group, and a $C_1$-$C_6$ alkanoyl group, and (iv) a 2-oxo-1,3-dioxolenemethylamino group which is substituted by a $C_1$-$C_6$ alkyl group; or a 1-piperidinyl group which may have 1 to 3 substituents selected from the group consisting of oxo, hydroxy, a halogen and a $C_1$-$C_6$ alkyl, and $R^3$ is a $C_1$-$C_6$ alkyl group, or a pharmaceutically acceptable salt thereof.

The benzoheterocyclic compounds of the formula [1] and salts thereof have excellent antibacterial activities against various gram positive and gram negative bacteria, and use useful for the treatment of various infectious diseases induced by various bacteria in human, other animals and fish and are also useful as an external antimicrobial or disinfectant agent for medical instruments or the like.

Prior Art

There are many literatures which disclose 4-oxoquinoline-3-carboxylic acid derivaties useful as antibacterial agents. Among these literatures, U.S. Pat. No. 4,563,459 (=German Pat. No. 3248507) discloses 1-cyclopropyl-dihydroquinoline carboxylic acid derivatives of the formula:

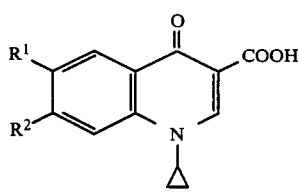

wherein $R_1$ is H, F, Cl, Br or $NO_2$, $R^2$ is H, Cl, F or $NR^3R^4$ wherein $R^3$ and $R^4$ together may form 5- or 6-membered saturated or partly unsaturated heterocycles.

European Patent Publication No. 153828 (=Japanese Patent First Publication (Kokai) No. 214777/1985) discloses 1-cyclopropyl-1,4-dihydro-4-oxoquinoline-3-carboxylic acid derivatives of the formula:

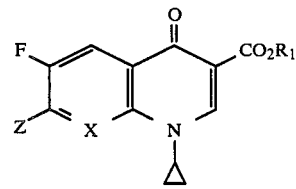

wherein Z is

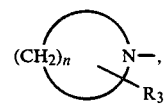

etc., X is CF or N, $R^1$ is H or lower alkyl.

U.S. Pat. No. 4,556,658 (=Japanese Patent First Publication (Kokai) No. 212474/1984) discloses 1-cyclopropyl-3-quinoline carboxylic acid derivatives of the formula:

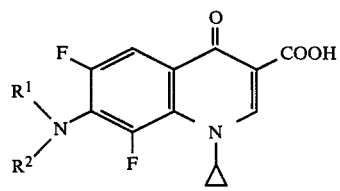

wherein $R^1R^2N$— may form heterocyclic groups.

Portugal Pat. No. 80546 (=European Patent Publication No. 195841) discloses quinolone carboxylic acid derivatives of the formula:

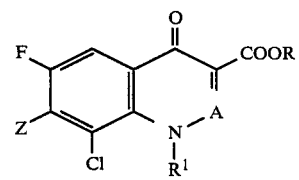

wherein A is N or CH, R is H or alkyl, $R^1$ is $C_3$-$C_6$ cycloalkyl, $R^2$ is H or $NH_2$, and Z is

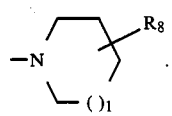

Similar 1-cyclopropyl-7-heterocyclic group-substituted dihydroquinoline carboxylic acid derivatives are also disclosed in other many literatures such as Japanese Patent First Publication (Kokai) Nos. 126082/1986 and 229877/1986, European Patent Publication Nos. 153163, 172651, 183129, 191451, 198192, and 202763, South African Pat. No. 8106080 and 8504792, U.S. Pat. No. 4,578,473, and U.K. Pat. 1,502,405.

BRIEF DESCRIPTION OF THE INVENTION

The object of the present invention is to provide novel benzoheterocyclic compounds of the formula [1] and salts thereof which have excellent antimicrobial activity and excellent absorbability. Another object of the invention is to provide a pharmaceutical composition containing as an active ingredient a compound of the formula [1] or a pharmaceutically acceptable salt thereof, which is useful for the treatment of various infectious diseases. These and other objects of the invention will be apparent to persons skilled in the art from the following description.

DETAILED DESCRIPTION OF THE INVENTION

The novel benzoheterocyclic compounds of the present invention have the formula [1] as mentioned above and include pharmaceutically acceptable salts thereof.

In the specification, the term "halogen atom" includes fluorine, chlorine, bromine or iodine atom.

The term "$C_1$–$C_6$ alkyl" includes straight chain or branched chain $C_1$–$C_6$ alkyl groups, such as methyl, ethyl, propyl, isopropyl, butyl, tert-butyl, pentyl, hexyl, etc.

The terms "a 1-pyrrolidinyl group which may have 1 to 3 substituents selected from the group consisting of (i) a $C_1$–$C_6$ alkyl group, (ii) an amino-($C_1$–$C_6$)alkyl group, said amino group being optionally substituted by 1 or 2 substituents selected from the group consisting of a $C_1$–$C_6$ alkyl group, a $C_1$–$C_6$ alkanoyl group, and $C_1$–$C_6$ alkoxycarbonyl group, (iii) an amino group which may be substituted by 1 or 2 substituents selected from the group consisting of a $C_1$–$C_6$ alkyl group, a phenyl($C_1$–$C_6$)alkyl group, a $C_1$–$C_6$ alkoxycarbonyl group, and a $C_1$–$C_6$ alkanoyl group, and (iv) a 2-oxo-1,3-dioxolenemethylamino group which is substituted by a $C_1$–$C_6$ alkyl group; or a 1-piperidinyl group which may have 1 to 3 substituents selected from the group consisting of oxo, hydroxy, a halogen and a $C_1$–$C_6$ alkyl" include, for example, 1-piperidinyl, 1-pyrrolidinyl, 4-methyl-1-piperidinyl, 4-ethyl-1-piperidinyl, 4-propyl-1-piperidinyl, 4-n-butyl-1-piperidinyl, 4-pentyl-1-piperidinyl, 4-hexyl-1-piperidinyl, 4-hydroxy-1-piperidinyl, 3-hydroxy-1-piperidinyl, 2-hydroxy-1-piperidinyl, 3,5-dimethyl-1-piperidinyl, 2,5-dimethyl-1-piperidinyl, 4-oxo-1-piperidinyl, 3-oxo-1-piperidinyl, 3-amino-1-pyrrolidinyl, 2-amino-1-pyrrolidinyl, 3-methylamino-1-pyrrolidinyl, 3-dimethylamino-1-pyrrolidinyl, 2-ethylamino-1-pyrrolidinyl, 3-propylamino-1-pyrrolidinyl, 2-n-butylamino-1-pyrrolidinyl, 3-pentylamino-1-pyrrolidinyl, 2-hexylamino-1-pyrrolidinyl, 3-diethylamino-1-pyrrolidinyl, 3-(N-methyl-N-propylamino)-1-pyrrolidinyl, 2-(N-ethyl-N-n-butylamino)-1-pyrrolidinyl, 3-acetylamino-1-pyrrolidinyl, 3-propionylamino-1-pyrrolidinyl, 2-butyrylamino-1-pyrrolidinyl, 3-pentanoylamino-1-pyrrolidinyl, 2-hexanoylamino-1-pyrrolidinyl, 3-aminomethyl-1-pyrrolidinyl, 3-(2-aminoethyl)-1-pyrrolidinyl, 2-(3-aminopropyl)-1-pyrrolidinyl, 3-(4-aminobutyl)-1-pyrrolidinyl, 3-(5-aminopentyl)-1-pyrrolidinyl, 3-(6-aminohexyl)-1-pyrrolidinyl, 3-(methylaminomethyl)-1-pyrrolidinyl, 3-(2-ethylaminoethyl)-1-pyrrolidinyl, 3-(3-propylaminopropyl)-1-pyrrolidinyl, 2-(4-n-butylaminobutyl)-1-pyrrolidinyl, 3-(5-pentylaminopentyl)-1-pyrrolidinyl, 3-(6-hexylaminohexyl)-1-pyrrolidinyl, 3-(dimethylaminomethyl)-1-pyrrolidinyl, 2-(N-methyl-N-ethyl-aminomethyl)-1-pyrrolidinyl, 3-(N-ethyl-N-n-butylaminomethyl)-1-pyrrolidinyl, 3-methylaminomethyl-4-methyl-1-pyrrolidinyl, 3-methylamino-4-methyl-1-pyrrolidinyl, 3-ethylaminomethyl-4-ethyl-1-pyrrolidinyl, 3-propylaminomethyl-5-propyl-1-pyrrolidinyl, 3-pentylaminomethyl-5-n-butyl-1-pyrrolidinyl, 3-n-butylamino-5-hexyl-1-pyrrolidinyl, 3-pentylamino-4-ethyl-1-pyrrolidinyl, 3-(5-methyl-2-oxo-1,3-dioxolen-4-yl)methylamino-1-pyrrolidinyl, 4-fluoro-1-piperidinyl, 3-amino-4-methyl-1-pyrrolidinyl, 2-oxo-1-piperidinyl, 3-acetylaminomethyl-1-pyrrolidinyl, 3-(N-ethyl-N-acetylamino)methyl-1-pyrrolidinyl, 3-t-butoxycarbonylaminomethyl-1-pyrrolidinyl, 3-ethylaminomethyl-1-pyrrolidinyl, 3-acetylaminomethyl-1-pyrrolidinyl, 3-(6-acetylaminohexyl)-1-pyrrolidinyl, 3-(4-pentyloxycarbonylaminobutyl)-1-pyrrolidinyl, 3-(5-hexyloxycarbonylaminopentyl)-1-pyrrolidinyl, 3-(N-t-butoxycarbonyl-N-ethylaminomethyl)-1-pyrrolidinyl, 3-(N-t-butoxycarbonyl-N-methylaminomethyl)-1-pyrrolidinyl, and the like.

The term "an amino-($C_1$–$C_6$)alkyl, said amino being optionally substituted by 1 or 2 substituents selected from the group consisting of $C_1$–$C_6$ alkyl group, a $C_1$–$C_6$ alkanoyl group, and a $C_1$–$C_6$ alkoxycarbonyl group" includes, for example, aminomethyl, 2-aminoethyl, 1-aminoethyl, 3-aminopropyl, 4-aminobutyl, 5-aminopentyl, 6-aminohexyl, 3-dimethylaminopropyl, 2-ethylaminoethyl, 4-propylaminobutyl, 5-n-butylaminopentyl, 6-pentylaminohexyl, methylaminomethyl, diethylaminomethyl, 2-dipropylaminoethyl, 1-di-n-butylaminoethyl, 3-dipentylaminopropyl, 4-dihexylaminobutyl, N-methyl-N-ethylaminoethyl, N-methyl-N-propylaminomethyl, formylaminomethyl, acetylaminomethyl, 2-propanoylaminoethyl, 3-butyrylaminopropyl, 4-pentanoylaminobutyl, 5-hexanoylaminopentyl, 6-acetylaminohexyl, propanoylaminomethyl, 1-acetylaminoethyl, 2-hexanoylaminoethyl, N-acetyl-N-methyaminomethyl, N-acetyl-N-ethylaminomethyl, methoxycarbonylaminomethyl, 2-ethoxycarbonylaminoethyl, 3-propoxycarbonylaminopropyl, 4-t-butoxycarbonylaminobutyl, 5-pentyloxycarbonylaminopentyl, 6-hexyloxycarbonylaminohexyl, t-butoxycarbonylaminomethyl, 2-t-butoxycarbonylaminoethyl, 1-t-butoxycarbonylaminoethyl, N-t-butoxycarbonyl-N-methylaminomethyl, N-t-butoxycarbonyl-N-ethylaminomethyl, and the like.

The term "$C_1$–$C_6$ alkanoyl" includes straight chain or branched chain $C_1$–$C_6$ alkanoyl groups, such as formyl, acetyl, propionyl, butyryl, pentanoyl, hexanoyl, and the like.

The term "an amino which may be substituted by 1 or 2 substituents selected from the group consisting of a $C_1$–$C_6$ alkyl and a $C_1$–$C_6$ alkanoyl" includes, for example, amino, methylamino, ethylamino, propylamino, t-butylamino, pentylamino, hexylamino, dimethylamino, diethylamino, di-n-propylamino, di-n-butylamino, dipentylamino, dihexylamino, N-methyl-N-n-butylamino, N-methyl-N-pentylamino, N-ethyl-N-hexylamino, acetylamino, formylamino, propionylamino, butyrylamino, pentanoylamino, hexanoylamino, N-methyl-N-acetylamino, N-ethyl-N-propionylamino, N-methyl-N-butyrylamino, N-n-propyl-N-pentanoylamino, N-ethyl-N-hexanoylamino, and the like.

The term "phenyl($C_1$–$C_6$)alkyl" includes, for example, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, and the like.

The term "$C_1$–$C_6$ alkoxycarbonyl" includes, for example, methoxycarbonyl, ethoxycarbonyl, propoxycarbonyl, isopropoxycarbonyl, butoxycarbonyl, tertbutoxycarbonyl, pentyloxycarbonyl, hexyloxycarbonyl, and the like.

The term "2-oxo-1,3-dioxolenemethylamino which is substituted by a $C_1$–$C_6$ alkyl" includes, for example, (5-methyl-2-oxo-1,3-dioxolen-4-yl)methylamino, (5-tert-butyl-2-oxo-1,3-dioxolen-4yl)methylamino, (5-pentyl-2-oxo-1,3-dioxolen-4-yl)methylamino, (5-hexyl-2-oxo-1,3-dioxolen-4-yl)methylamino, (5-ethyl-2-oxo-1,3-dioxolen-4-yl)methylamino, (5-propyl-2-oxo-1,3-dioxolen-4-yl)methylamino, and the like.

The compounds of the present invention of the above general formula [1] can be prepared by various processes and preferably prepared, for example, by the processes as shown in the following reaction schemes.

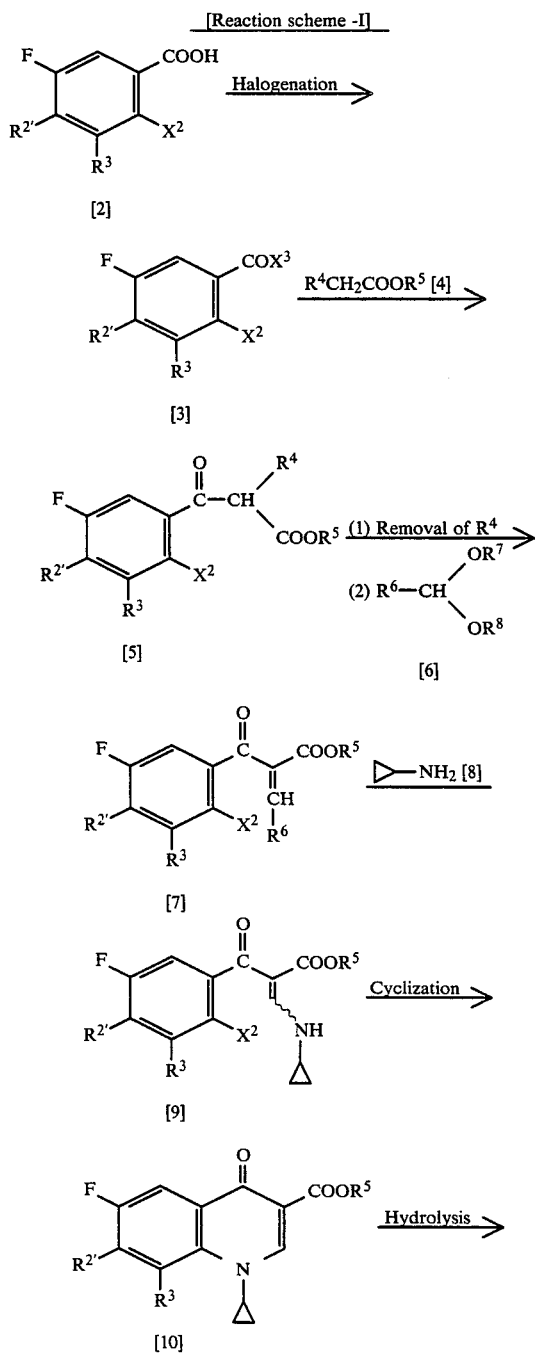

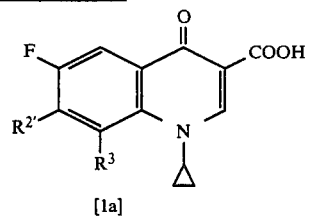

-continued
[Reaction scheme -I]

wherein $R^2$ and $R^3$ are as defined above, $R^{2'}$ is a halogen atom or a $R^2$ group ($R^2$ is as defined above), $R^4$ is a group of the formula: —$COR^9$ (wherein $R^9$ is a lower alkyl) or a group of the formula: —$COOR^{10}$ (wherein $R^{10}$ is a lower alkyl), $R^5$ is a lower alkyl, $R^6$ is a group of the formula:

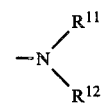

(wherein $R^{11}$ and $R^{12}$ are each a lower alkyl) or a lower alkoxy, $X^2$ and $X^3$ are each a halogen atom, $R^7$ and $R^8$ are each a lower alkyl.

The halogenation of the compound [2] is carried out by reacting with a halogenating agent in the presence or absence of a solvent. The solvent includes aromatic hydrocarbons (e.g. benzene, toluene, xylene, etc.), halogenated hydrocarbons (e.g. dichloromethane, chloroform, carbon tetrachloride, etc.), ethers (e.g. dioxane, tetrahydrofuran, diethyl ether, etc.), dimethylformamide (DMF), dimethyl sulfoxide (DMSO), and the like. The halogenating agent may be any conventional halogenating agents which can convert hydroxy in carboxy group into a halogen atom, and includes, for example, thionyl chloride, phosphorus oxychloride, phosphorus oxybromide, phosphorus pentachloride, phosphorus pentabromide, and the like. The amounts of the compound [2] and the halogenating agent are not specified, but, in case of using no solvent, the halogenating agent is usually used in a large excess amount, and in case of using a solvent, the halogenating agent is usually used in an amount of at least 1 mole, preferably 2 or 4 moles, per 1 mole of the compound [2]. The reaction temperature and the reaction period of time are not specified, either, but the reaction is usually carried out at a temperature of from room temperature to 100° C. for 30 minutes to 6 hours.

The reaction of the compound [3] and the compound [4] is carried out in a suitable solvent in the presence of a basic compound. The solvent may be any conventional solvents unless they give any undesirable effect on the reaction, and includes, for example, water, ethers (e.g. diethyl ether, dioxane, tetrahydrofuran, monoglyme, diglyme, etc.), alcohols (e.g. methanol, ethanol, isopropanol, etc.), aromatic hydrocarbons (e.g. benzene, toluene, xylene, etc.), aliphatic hydrocarbons (e.g. n-hexane, heptane, cyclohexane, ligroin, etc.), amines (e.g. pyridine, N,N-dimethylaniline, etc.), halogenated hydrocarbons (e.g. chloroform, dichloromethane, carbon tetrachloride, etc.), aprotic polar solvents (e.g. DMF, DMSO, hexamethylphosphoramide (HMPA), etc.), and a mixture of these solvents. The basic compound includes inorganic bases (e.g. metallic sodium, metallic potassium, metallic magnesium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, etc.), and organic bases (e.g. pyridine, piperidine, quinoline, triethylamine, N,N-dimethylaniline, etc.). The reaction is usually carried out at a temperature of from 0° to 150° C., preferably from room temperature to 120° C., for 0.5 to 15 hours. The compound [4] is usually used in an amount of at least 1 mole, preferably 1 to 2 moles, per 1 mole of the compound [3]. The basic compound is usually used in an amount of at least 1 mole, preferably 1 to 2 moles, per 1 mole of the compound [3].

The compound [5] wherein $R^4$ is the group: —$COR^9$ is subjected to the reaction for removal of the group: —$COR^9$ in a suitable solvent in the presence of a basic compound. The solvent includes ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), aprotic polar solvents (e.g. DMF, DMSO, HMPA, etc.), and the like. The basic compound includes ammonia gas, aqueous ammonia, primary or secondary amines (e.g. ethylamine, diethylamine, piperidine, etc.), and the like. The reaction is usually carried out at a temperature of from 0° to 150° C., preferably from room temperature to 100° C., for 1 to 20 hours.

The compound [5] wherein $R^4$ is a group: —$COOR^{10}$ is subjected to the reaction for removal of the group: —$COOR^{10}$ in an aqueous solution in the presence of an acid catalyst. The acid catalyst includes mineral acids (e.g. hydrochloric acid, sulfuric acid, etc.) and organic acids (e.g. p-toluenesulfonic acid, etc.). The reaction is usually carried out at a temperature of from 0° to 150° C., preferably from room temperature to 100° C., for 1 to 20 hours.

The reaction of the $R^4$ group-removed compound and the compound [6] is carried out in a suitable solvent. The solvent may be any solvents which are used in the above reaction for the removal of the $R^4$ group. The reaction is usually carried out at a temperature of from 0° to 200° C., preferably from 0° to 150° C., for 0.5 to 10 hours. The comound [6] is usually used in an equimolar to large excess amount, preferably 1 to 2 moles per 1 mole of the compound [5]. In case of using a compound [6] wherein $R^6$ is a lower alkoxy group, the reaction may also be carried out by using acid anhydrides (e.g. acetic anhydride) as a solvent as well as above-mentioned solvents at a temperature of from 0° to 200° C., preferably 0° to 170° C.

The reaction of the compound [7] and the compound [8] is carried out in a suitable solvent. The solvent may be any conventional solvents unless they give any undesirable effect on the reaction, and includes, for example, alcohols (e.g. methanol, ethanol, propanol, etc.), ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The reaction is usually carried out at a temperature of from 0° to 150° C., preferably from room temperature to 100° C., for 0.5 to 15 hours. The compound [8] is usually used in an amount of at least 1 mole, preferably 1 to 2 moles, per 1 mole of the compound [7]. In the reaction, a basic compound may optionally be added and such basic compound may be any basic compounds which are used in the above reaction of the compound [3] and the compound [4].

The cyclization of the compound [9] is carried out in a suitable solvent in the presence of a basic compound. The solvent may be any conventional solvents unless they give any undesirable effect on the reaction, and includes, for example, ethers (e.g. diethyl ether, dioxane, tetrahydrofuran, monoglyme, diglyme, etc.), aliphatic hydrocarbons (e.g. n-hexane, heptane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The basic compound includes inorganic bases (e.g. metallic sodium, metallic potassium, sodium hydride, sodium amide, sodium hydroxide, potassium hydroxide, etc.), metal alcoholates (e.g. sodium methylate, sodium ethylate, etc.), and organic bases (e.g. 1,8-diazobicyclo[5.4.0]undecene-7 (DBU), N-benzyltrimethylammonium hydroxide, tetrabutylammonium hydroxide, etc.). The reaction is usually carried out at a temperature of from 0° to 150° C., preferably from room temperature to 120° C., for 0.5 to 5 hours. The basic compound is usually used in an amount of at least 1 mole, preferably 1 to 2 moles, per 1 mole of the compound [9].

The hydrolysis of the compound [10] can be carried out under the conditions of conventional hydrolysis, for instance, in the presence of a basic compound (e.g. sodium hydroxide, potassium hydroxide, barium hydroxide, potassium carbonate, etc.), a mineral acid (e.g. sulfuric acid, hydrochloric acid, nitric acid, etc.) or an organic acid (e.g. acetic acid, aromatic sulfonic acids, etc.) in a solvent such as water, alcohols (e.g. methanol, ethanol, isopropanol, etc.), ketones (e.g. acetone, methyl ethyl ketone, etc.), ethers (e.g. dioxane, ethylene glycol, etc.), acetic acid, or a mixture thereof. The reaction is usually carried out at a temperature of from room temperature to 200° C., preferably from room temperature to 150° C., for 0.1 to 30 hours. By the reaction, there is produced the compound [Ia].

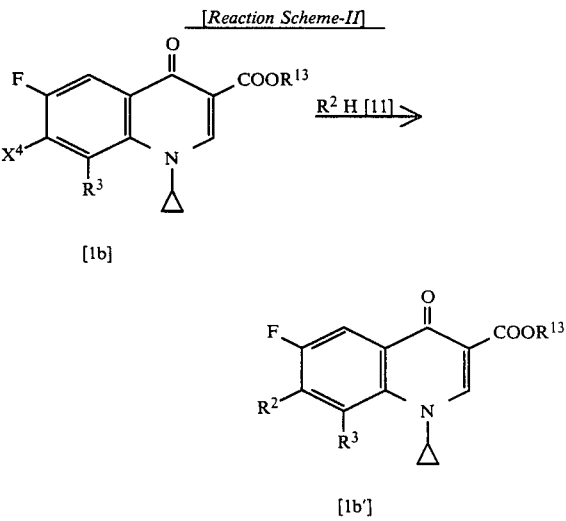

wherein $R^2$ and $R^3$ are as defined above, $X^4$ is a halogen atom, and $R^{13}$ is hydrogen atom or a group of the formula:

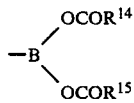

(wherein $R^{14}$ and $R^{15}$ are each an alkyl).

The reaction of the compound [1b] and the compound [11] is carried out in an inert solvent, wherein both compounds are used in a wide range of ratio, and the compound [11] is usually used in an amount of at least 1 mole, preferably 1 to 5 moles, per 1 mole of the compound [1b]. The solvent includes, for example, water, alcohols (e.g. methanol, ethanol, isopropanol, butanol, amyl alcohol, isoamyl alcohol, etc.), aromatic hydrocarbons (e.g. benzene, toluene, xylene, etc.), ethers (e.g. tetrahydrofuran, dioxane, diglyme, etc.), dimethylacetamide, DMF, DMSO, HMPA, N-methylpyrrolidone, and a mixture thereof. Among these solvents, the preferred one is DMF, DMSO, HMPA, and N-methylpyrrolidone. The reaction may also be carried out in the presence of an acid-removing agent, such as inorganic carbonates (e.g. sodium carbonate, potassium carbonate, sodium hydrogen carbonate, potassium hydrogen carbonate, etc.) or organic bases (e.g. pyridine, quinoline, triethylamine, etc.). An alkaline methal halide (e.g. potassium fluoride, etc.) may also be added in the reaction mixture. The reaction is usually carried out under a pressure of from 1 to 2 atm., preferably from 1 to 10 atm., at a temperature of from room temperature to 250° C., preferably from room temperature to 200° C., for 0.5 to 30 hours.

The compound [1b'] wherein $R^{13}$ is a group:

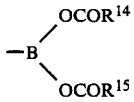

can be converted into the corresponding compound [1b'] wherein $R^{13}$ is hydrogen atom by treating the former compound with an acid or a base to decompose the chelate compound. The acid includes mineral acids (e.g. hydrochloric acid, sulfuric acid, etc.) and organic acids (e.g. acetic acid, p-toluenesulfonic acid, etc.) and the base includes mineral bases (e.g. sodium hydroxide, potassium hydroxide, sodium hydrogen carbonate, potassium hydrogen carbonate, potassium carbonate, etc.) and organic bases (e.g. triethylamine, etc.). The reaction is preferably carried out at a temperature of from 0° C. to 150° C., preferably from 0° C. to 100° C. The acid or the base may be used in an amount of at least 1 mole, preferably 1 to 10 moles, per 1 mole of the starting compound.

In the reaction scheme-I, the starting compounds of the formula [2] are novel or known compounds, which can be prepared, for example, by the process as shown in the following reaction scheme-V.

[Reaction scheme-V]

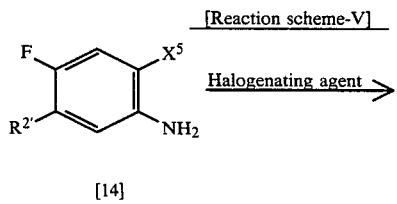

-continued
[Reaction scheme-V]

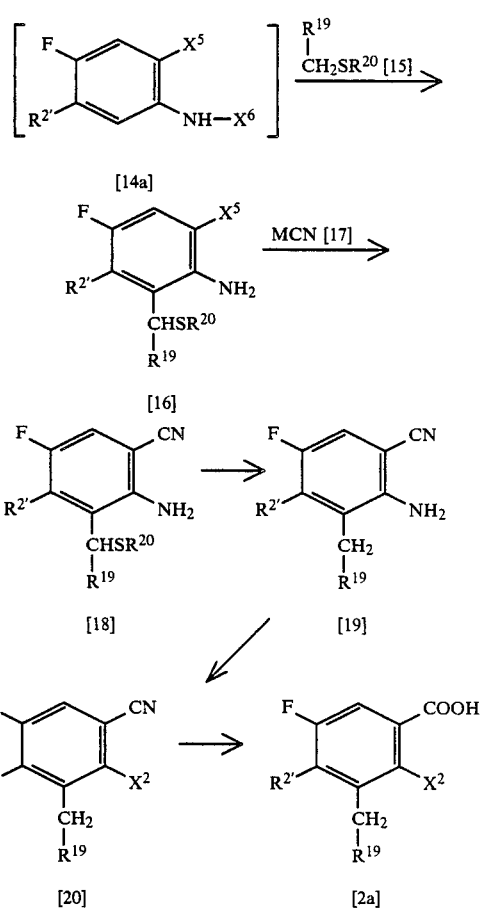

wherein $R^{2'}$ and $X^2$ are as defined above, $X^5$ and $X^6$ are each a halogen atom, $R^{19}$ is hydrogen atom or a lower alkyl and $R^{20}$ is a lower alkyl, in which $R^{19}$ and $R^{20}$ may be taken together to form a 5- to 7-membered ring, and M is an alkaline metal (e.g. sodium, potassium, etc.) or a metal (e.g. silver, calcium, copper, etc.).

In case that $R^{19}$ and $R^{20}$ of the compound [16] are taken together to form a 5- to 7-membered ring, $R^{19}$ of the compound [20] is -$R^{19}$-$R^{20}$-H.

The compound [16] can be prepared by reacting a starting aniline derivative of the formula [14] with a halogenating agent and then reacting the resultant compound of the formula [14a] with a thio compound of the formula [15].

The reaction of an aniline derivative [14] and a halogenating agent is usually carried out in a suitable solvent. The solvent may be any conventional solvents unless they give any undesirable effect on the reaction, and includes, for example, halogenated hydrocarbons (e.g. chloroform, dichloromethane, etc.), ethers (e.g. dioxane, diethyl ether, tetrahydrofuran, etc.), aromatic hydrocarbons (e.g. benzene, toluene, xylene, etc.), lower alcohols (e.g. methanol, ethanol, isopropanol, etc.), and polar solvents (e.g. DMSO, HMPA, acetonitrile, etc.). The halogenating agent may be any conventional halogenating agents and includes, for example, N-bromosuccinimide, N-chlorosuccinimide, sodium hypobromite, sodium hypochlorite, bleaching powder, thionyl chloride, tert-butyl hypochlorite, and the like.

The halogenating agent is usually used in an amount of at least 1 mole, preferably 1 to 6 moles, per 1 mole of the starting material. The reaction is usually carried out at a temperature of from −78° C. to room temperature, preferably from −60° to 15° C., and usually completes within a few minutes. By the reaction, there is produced the intermediate of the formula [14a]. While the resultant compound [14a] may be separated from the reaction mixture to provide it for a subsequent reaction, the reaction mixture is usually provided for the reaction with a thio compound of the formula [15] without separating it from the reaction mixture.

The reaction of the compounds [14a] and the compound [15] is carried out in the same solvent as above-mentioned in the presence of a basic compound. The basic compound includes inorganic bases (e.g. potassium carbonate, sodium carbonate, sodium hydroxide, sodium hydrogen carbonate, sodium amide, sodium hydride, etc.), and organic bases such as tertiary amines (e.g. triethylamine, tripropylamine, pyridine, quinoline, etc.). The compound [15] is usually used in an amount of at least 1 mole, preferably 1 to 1.5 moles, per 1 mole of the compound [14a]. The reaction is usually carried out at a temperature of from room temperature to 150° C., preferably from room temperature to 100° C., for 1 to 50 hours. The reaction of the compound [16] and the compound [17] is carried out in a suitable solvent in the presence or absence of a basic compound. The solvent includes water, alcohols (e.g. methanol, ethanol, isopropanol, etc.), aromatic hydrocarbons (e.g. benzene, toluene, xylene, etc.), ethers (e.g. dioxane, tetrahydrofuran, diglyme, etc.), polar solvents (e.g. DMF, DMSO, HMPA, N-methylpyrrolidone, etc.), or a mixture thereof. The basic compound includes inorganic carbonates (e.g. sodium carbonate, potassium carbonate, sodium hydrogen carbonate, potassium hydrogen carbonate, etc.), organic bases (e.g. pyridine, quinoline, triethylamine, etc.), phase transition catalysts (e.g. phenyltriethylammonium chloride, tetramethylammonium chloride, etc.), and the like. The compound [17] is usually used in an amount of at least 1 mole, preferably 1 to 2 moles, per 1 mole of the compound [16]. The reaction is usually carried out at a temperature of from room temperature to 200° C., preferably from room temperature to 180° C., for 0.5 to 10 hours.

The desulfuration of the compound [18] for preparing the compound [19] is usually carried out in a solvent in the presence of a suitable catalyst. The catalyst includes, for example, aluminum-amalgam, lithium-lower alkylamine, Raney nickel, Raney cobalt, triethyl phosphite, triphenyl phosphine, and the like, and preferable one is Raney nickel. The solvent includes alcohols (e.g. methanol, ethanol, isopropanol, etc.), ethers (e.g. diehtyl ether, dioxane, tetrahydrofuran, etc.), and the like. The reaction is usually carried out at a temperature of from 0° to 200° C., preferably from room temperature to 100° C., for 10 minutes to 5 hours. The catalyst is usually used in an amount of from 1 to 10-fold by weight of the compound [18].

The reaction of converting the compound [19] into the compound [20] is carried out by reacting the compound [19] with a metallic salt of nitrous acid (e.g. sodium nitrite, potassium nitrite, etc.) in a suitable solvent in the presence of an acid, and then reacting the resultant product with a metal halide (e.g. potassium iodide, copper (I) chloride, copper (I) bromide, etc.) without separating it from the reaction mixture. The acid includes mineral acids such as hydrochloric acid, sulfuric acid and hydrobromic acid. The solvent includes water, alkanoic acids (e.g. acetic acid, etc.), ethers (e.g. dioxane, tetrahydrofuran, etc.), aromatic hydrocarbons (e.g. benzene, toluene, xylene, etc.), alcohols (e.g. methanol, ehtanol, isopropanol, etc.), halogenated hydrocarbons (e.g. chloroform, dichloromethane, dichloroethane, etc.), aprotic polar solvents (e.g. DMF, DMSO, HMPA, etc.), and a mixture thereof. The metallic salt of nitrous acid and the metal halide each is usually used in an amount of at least 1 mole, preferably 1 to 1.5 moles, per 1 mole of the compound [19]. The reaction is usually carried out at a temperature of from 0° to 150° C., preferably from 0° to 100° C., for 10 minutes to 5 hours.

The hydrolysis of the compound [20] can be carried out in the presence of a suitable hydrolysis catalyst, for instance, a mineral acid (e.g. sulfuric acid, hydrochloric acid, hydrobromic acid, phosphoric acid, etc.) or a basic compound (e.g. sodium hydroxide, potassium hydroxide, sodium carbonate, potassium carbonate, sodium hydrogen carbonate, etc.) in the presence or absence of a solvent. The solvent includes, for example, water and a mixture of water and a lower alcohol (e.g. methanol, ehtanol, etc.). The reaction is usually carried out at a temperature of from 50° to 200° ]C., preferably 70° to 180° C., for 1 to 10 hours.

In the reaction scheme-II, the compounds of the formula [1b] wherein $R^{13}$ is a group:

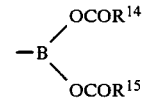

can be prepared, for example, by the process as shown in the following reaction scheme-VI.

[Reaction scheme-VI]

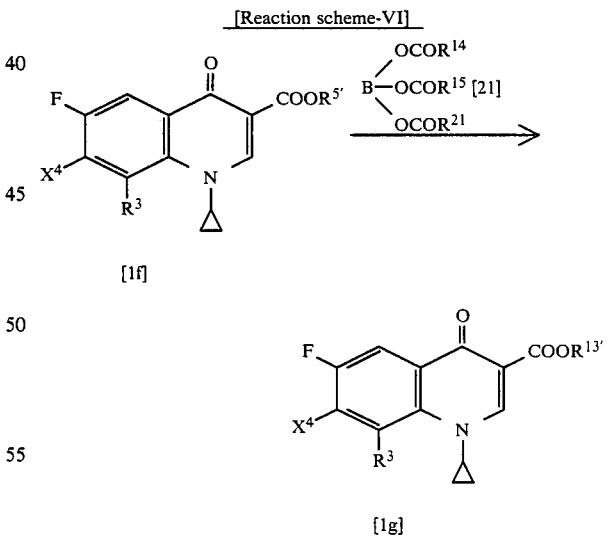

wherein $R^3$, $X^4$, $R^{14}$ and $R^{15}$ are as defined above, $R^{5'}$ is a lower alkyl or hydrogen atom, $R^{13'}$ is a group:

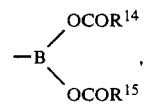

and $R^{21}$ is a lower alkyl.

The reaction of the compound [1f] and the compound [21] is carried out in a suitable solvent. The solvent includes, for example, the solvents employed in the reaction of the $R^4$ group-removed compound and the compound [6] in the above reaction scheme-I. The reaction is usually carried out at a temperature of from room temperature to 200° C., preferably from room temperature to 150° C., for 10 minutes to 5 hours. The compound [21] is usually used in an amount of at least 1 mole, preferably 1 to 10 moles, per 1 mole of the compound [1f].

The compound [1] in which the 1-pyrrolidinyl group is substituted by amino can be converted into the compound [1] in which the 1-pyrrolidinyl group is substituted by a group:

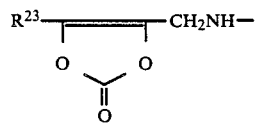

the above reaction scheme-II, and the compound [1] in which the 1-pyrrolidinyl group is substituted by a group:

can also be converted into the compound [1] in which 1-pyrrolidinyl group is substituted by amino, by hydrolyzing the former compound under the same reaction condition as employed in the hydrolysis of the above compound [10].

[Reaction scheme-IX]

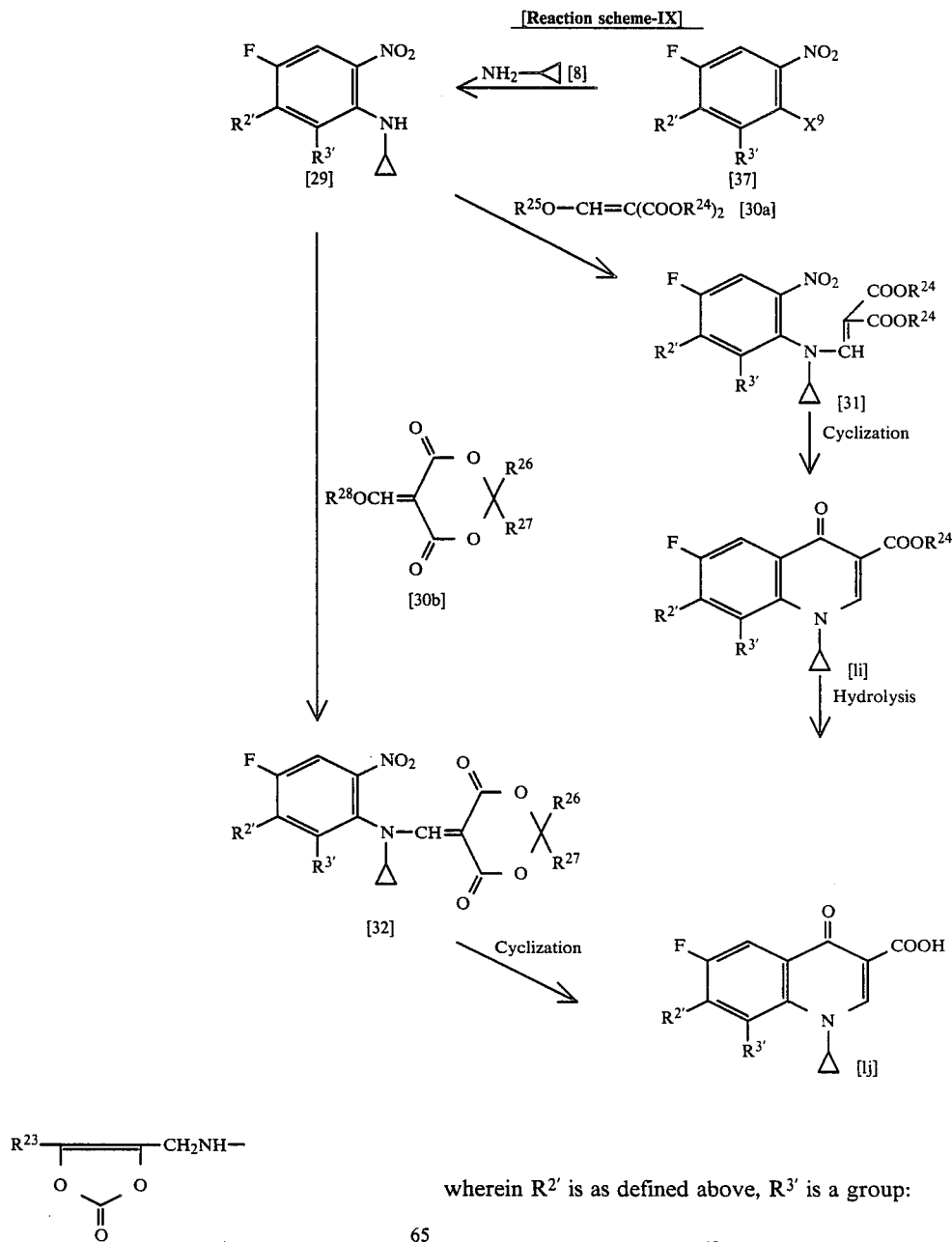

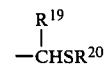

using the same reaction condition as employed in the reaction of the compound [1b] and the compound [11] in wherein $R^{2'}$ is as defined above, $R^{3'}$ is a group:

$$-\overset{R^{19}}{\underset{|}{C}}HSR^{20}$$

(wherein $R^{19}$ and $R^{20}$ are as defined above) or $R^3$ (wherein $R^3$ is as defined above), $R^{24}$, $R^{25}$, $R^{26}$, $R^{27}$ and $R^{28}$ are each a lower alkyl, and $X^9$ is a halogen atom.

The reaction of the compound [37] and the compound [8] can be carried out under the same reaction condition as employed in the reaction of the compound [1b] and the compound [11] in the above reaction scheme-II.

The reaction of the compound [29] and the compound [30a] or [30b] is carried out in the presence or absence of a solvent, preferably in the absence of any solvent. The solvent includes, for example, alcohols, (e.g. methanol, ethanol, isopropanol, etc.), aromatic hydrocarbons (e.g. benzene, toluene, etc.), polar solvents (e.g. acetonitrile, DMF, DMSO, HMPA, etc.). The compound [30a] or [30b] is usually used in an amount of at least 1 mole, preferably 1 to 1.5 moles, per 1 mole of the compound [29]. The reaction is usually carried out at a temperature of from room temperature to 200° C., preferably from 60° to 200° C., for 0.5 to 25 hours.

The cyclization of the compound [31] or [32] can be carried out according to various known methods such as a heating method, a method using an acidic compound (e.g. phosphorus oxychloride, phosphorus pentachloride, phosphorus trichloride, thionyl chloride, conc. sulfuric acid, polyphosphoric acid, etc.). In case of using the heating method, the reaction is usually carried out in a high b.p. solvent such as a high b.p. hydrocarbon or a high b.p. ether (e.g. tetralin, diphenyl ether, diethylene glycol dimethyl ether, etc.) at a temperature of from 100° to 250° C., preferably from 150° to 200° C. In case of using the method using an acidic compound, the acidic compound is usually used in an equimolar to a large excess amount, preferably 10 to 20 moles, per 1 mole of the compound [31] or [32], and the reaction is usually carried out in the presence or absence of a suitable solvent at a temperature of from room temperature to 150° C. for 0.1 to 6 hours. The solvent includes acid anhydrides (e.g. acetic anhydride, etc.) in addition to the solvents employed in the cyclization of the above compound [9].

The hydrolysis of the compound [1i] can be carried out under the same reaction condition as employed in the hydrolysis of the compound [10] in the above reaction scheme-I.

The compound [1j] in which $R^{3'}$ is a group:

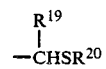

can be coverted into the corresponding compound in which $R^{3'}$ is $-CH_2R^{19}$ by treating the former compound under the same reaction condition as employed in the reaciton wherein the compound [18] is converted into the compound [19] in the above reaction scheme-V.

The compound [29] employed as the starting material in the above reaciton scheme-IX can be prepared, for example, by the processes as shown in the following reaction schemes-X to XII.

[Reaction scheme-X]

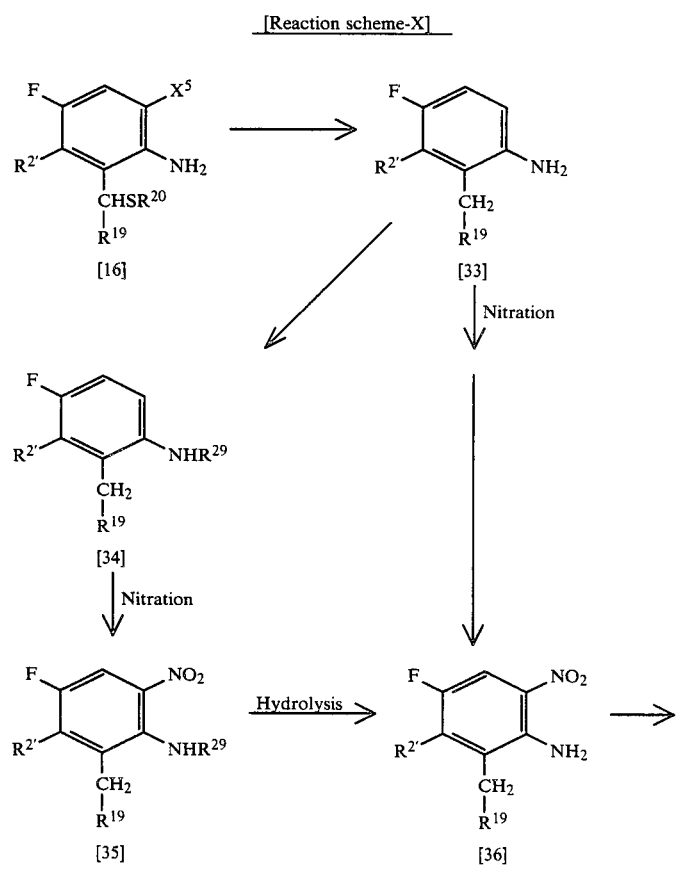

[Reaction scheme-X]

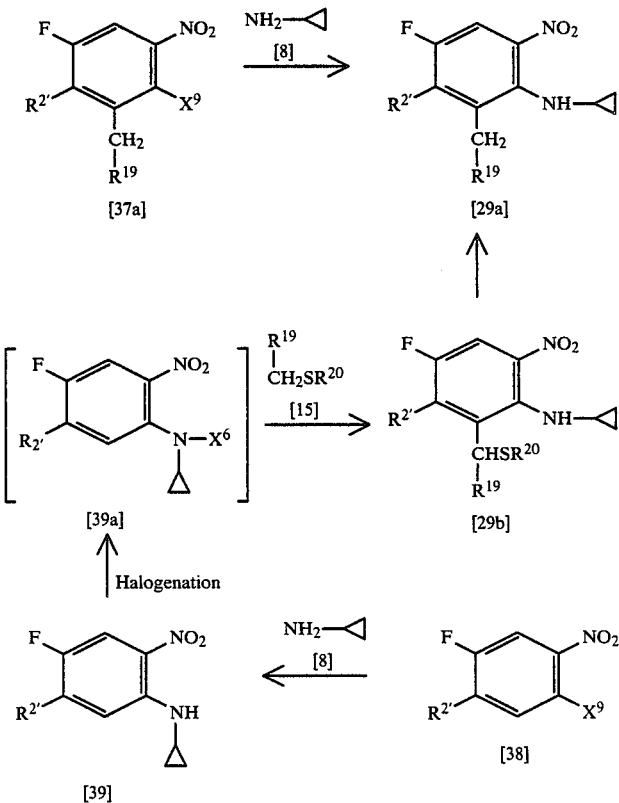

wherein $R^{2'}$, $R^{19}$, $R^{20}$ and $X^6$ are as defined above, $R^{29}$ is a (lower) alkanoyl, and $X^9$ is a halogen atom.

The desulfuration of the compound [16] or [29b] can be carried out under the same reaction conditions as employed in the desulfuration of the above compound [18].

The reaction of converting the compound [33] into the compound [34] is carried out in the presence of a (lower) alkanoylating agent such as a (lower) alkanoic acid (e.g. formic acid, acetic acid, propionic acid, etc.), a (lower) alkanoic acid anhydride (e.g. acetic anhydride, etc.), a (lower) alkanoic acid halide (e.g. acetyl chloride, propionyl bromide, etc.), or the like. In case of using an acid anhydride or an acid halide as the (lower) alkanoylating agent, a basic compound may be employed. The basic compound includes, for example, alkali metals (e.g. metallic sodium, metallic potassium, etc.), and hydroxides, carbonates or hydrogen carbonates thereof, organic bases (e.g. pyridine, piperidine, etc.), and the like. The reaction is carried out in the presence or absence of a solvent, usually in the presence of a suitable solvent. The solvent includes, for example, ketones (e.g. acetone, methyl ethyl ketone, etc.), ethers (e.g. diethyl ether, dioxane, etc.), aromatic hydrocarbons (e.g. benzene, toluene, xylene, etc.), acetic acid, acetic anhydride, water, pyridine, and the like. The (lower) alkanoylating agent is used in an amount of at least 1 mole per 1 mole of the compound [33], usually in equimolar to a large excess amount. The reaction is usually carried out at a temperature of from 0° to 150° C., preferably from 0° to 100° C., for 5 minutes to 10 hours. In case of using a (lower) alkanoic acid as the (lower) alkanoylating agent, a dehydrating agent is preferably employed. The dehydrating agent includes mineral acids (e.g. sulfuric acid, hydrochloric acid, etc.), sulfonic acids (e.g. p-toluenesulfonic acid, benzenesulfonic acid, ethanesulfonic acid, etc.), and the like. The reaction is preferably carried out at a temperature of from 50° to 120° C.

The nitration of the compound [33] or [34] is carried out by treating the said compound with a nitrating agent such as fuming nitric acid, conc. nitric acid, a mixed acid (e.g. nitric acid plus sulfuric acid, fuming sulfuric acid, phosphoric acid or acetic anhydride, etc.), an alkali metal nitrate plus sulfuric acid, an anhydride of nitric acid and an organic acid (e.g. acetyl nitrate, benzoyl nitrate, etc.), nitrogen tetraoxide, nitric acid plus mercury nitrate, nitrate of acetone cyanohydrin, an alkyl nitrate plus sulfuric acid or a polyphosphoric acid, or the like, in the presence or absence of a solvent such as acetic acid, acetic anhydride, sulfuric acid, or the like. The nitrating agent is preferably used in an amount of 1 to 1.5 moles per 1 mole of compound [33] or [34]. The reaction is usually carried out at a temperature of from −10° to 70° C. for 1 to 24 hours.

The hydrolysis of the compound [35] is carried out under the same reaction conditions as employed in the hydrolysis of the above compound [10].

The reaction of the compound [37a] or [38] with the compound [8] can be carried out under the same reaction conditions as employed in the reaction of the compound [1b] and the compound [11] in the above reaction scheme-II.

The halogenation of the compound [39] can be carried out under the same reaction conditions as employed in the halogenation of the above compound [14].

The reaction of the compound [39a] and the compound [15] can be carried out under the same reaction conditions as employed in the reaction of the compound [14a] and the compound [15].

The convertion of the compound [29b] into the compound [29a] can be carried out under the same conditions as in the convertion of the compound [18] into the compound [19].

The reaction of converting the compound [36] into the compound [37] can be carried out by converting the former compound into a diazonium salt thereof using sodium nitrite and an acid (e.g. sulfuric acid, hydrochloric acid hydrobromic acid, boron fluoride, etc.) in a solvent such as a (lower) alkanoic acid (e.g. acetic acid), water, etc., and then reacting the diazonium salt with a copper powder or a copper halide (e.g. cuprous bromide, cuprous chloride, cupric chloride, etc.) in the presence of a hydrohalogenic acid (e.g. hydrobromic acid, hydrochloric acid, etc.), or with potassium iodide in the presence or absence of a copper powder, preferably with a copper halide in the presence of a hydrohalogenic acid. The sodium nitrite is usually used in an amount of 1 to 2 moles, preferably 1 to 1.5 moles, per 1 mole of the compound [36], and the copper halide is usually used in an amount of 1 to 5 moles, preferably 1 to 4 moles, per 1 mole of the compound [36]. The reaction is usually carried out at a temperature of from $-20°$ to $100°$ C., preferably from $-5°$ to $100°$ C., for 10 minutes to 5 hours.

The halogen atom of $X^9$ in the compound [37a] can be converted into each other.

[Reaction scheme-XI]

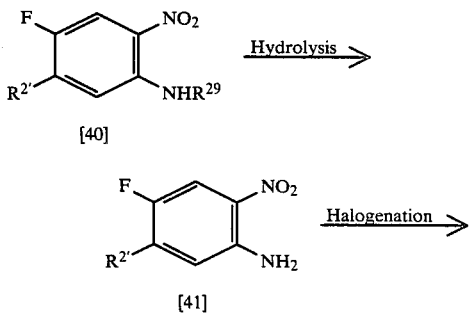

[Reaction scheme-XI]
-continued

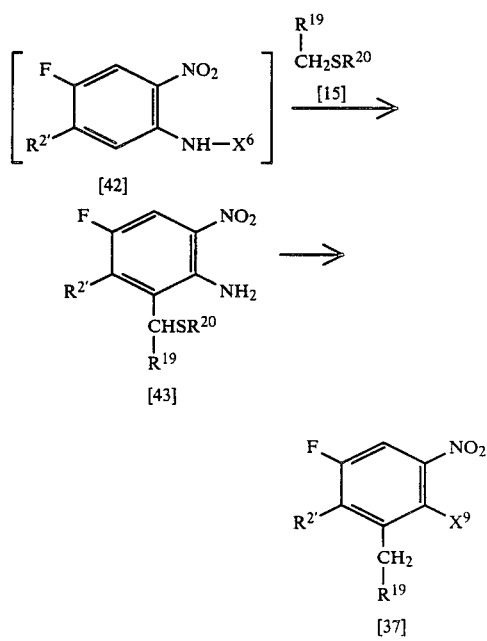

wherein $R^{2'}$, $R^{19}$, $R^{20}$, $R^{29}$, $X^6$ and $X^9$ are as defined above.

The hydrolysis of the compound [40] can be carried out under the same reaction conditions as employed in the hydrolysis of the above compound [10].

The halogenation of the compound [41] can be carried out under the same reaction conditions as employed in the halogenation of the compound [14] in the above reaction scheme-V.

The reaction of the compound [42] and the compound [15] can be carried out under the same reaction conditions as employed in the reaction of the compound [14a] and the compound [15].

The desulfuration of the compound [43] can be carried out under the same reaction conditions as employed in the desulfuration of the compound [18] in the above reaction scheme-V.

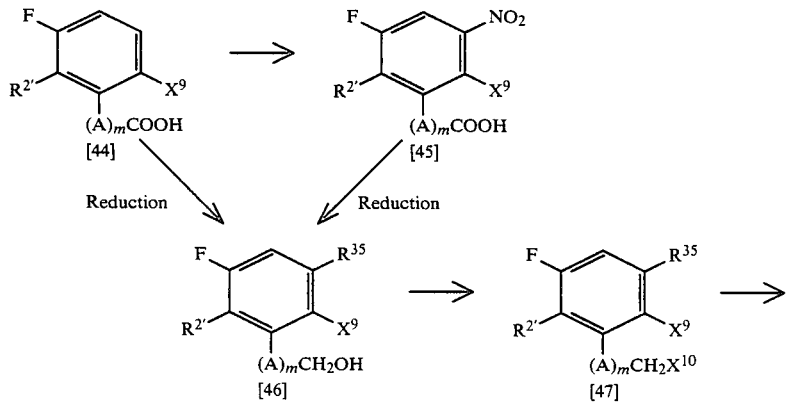

[Reaction scheme-XII]

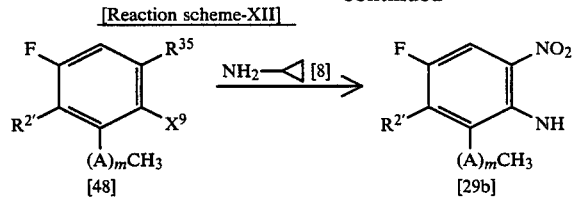

wherein $R^{2'}$ and $X^9$ are as defined above, A is a (lower) alkylene, m is 0 or 1, $X^{10}$ is a halogen atom, or a phenylsulfonyloxy which may be substituted by a lower alkyl, and $R^{35}$ is hydrogen atom or nitro group.

The nitration of the compound [44] in the above reaction scheme-XII can be carried out under the same reaction conditions as employed in the nitration of the compound [34] in the above reaction scheme-X.

The reaction of the compound [44] or [45] is usually carried out using a hydride reducing agent such as sodium borohydride, lithium abluminum hydride or diborane, and the reducing agent is usually used in an amount of at least 1 mole, preferably 1 to 3 moles, per 1 mole of the compound [44] or [45]. The reduction reaction is usually carried out in a suitable solvent, for example, water, (lower) alcohols (e.g. methanol, ethanol, isopropanol, etc.), ethers (e.g. tetrahydrofuran, diethyl ether, diglyme, etc.), DMSO, or the like, at a temperature of from $-60°$ to $80°$ C., preferably from $-30°$ C. to $50°$ C., for 10 minutes to 15 hours. In case of using lithium aluminum hydride or diborane as a reducing agent, an anhydrous solvent such as diethyl ether, tetrahydrofuran or diglyme is preferably employed.

The reaction of converting the compound [46] into the compound [47] wherein $X^{10}$ is a halogen atom by halogenation is carried out under any reaction conditions usually employed in halogenation of hydroxy group, and may be carried out, for example, by reacting the compound [46] with a halogenating agent in the presence or absence of a suitable inert solvent. The halogenating agent includes, for example, hydrohalogenic acids (e.g. hydrochloric acid, hydrobromic acid, etc.), N,N-diethyl-1,2,2-trichlorovinylamide, phosphorus pentachloride, phosphorus pentabromide, phosphorus oxychloride, thionyl chloride, diethylaminosulfur trifluoride (DAST), and the like. The inert solvent includes, for example, ethers (e.g. dioxane, tetrahydrofuran, etc.), halogenated hydrocarbons (e.g. chloroform, dichloromethane, carbon tetrachloride, etc.), and the like. The halogenating agent is used in an amount of at least 1 mole per 1 mole of the compound [46], usually in an equimolar to an excess amount, the reaction is usually carried out at a temperature of from $0°$ to $150°$ C., preferably from $0°$ to $80°$ C., for 10 minutes to 15 hours. In case of using DAST as a halogenating agent, a basic compound such as triethylamine may be employed.

When the compound [46] is reacted with a phenylsulfonyl halide which may have a lower alkyl substituent on the phenyl ring, it may be converted into a compound [47] wherein $X^{10}$ is a phenylsulfonyloxy which may be substituted with a lower alkyl. The reaction can be carried out in a suitable solvent in the presence of a basic compound.

The solvent used in the above method includes, for example, ethers (e.g. diethyl ether, dioxane, tetrahydrofuran, monoglyme, diglyme, etc.), alcohols (e.g. methanol, ethanol, isopropanol, etc.), aromatic hydrocarbons (e.g. benzene, toluene, xylene, etc.), aliphatic hydrocarbons (e.g. n-hexane, heptane, cyclohexane, ligroin, etc.), amines (e.g. pyridine, N,N-dimethylaniline, etc.), halogenated hydrocarbons (e.g. chloroform, dichloromethane, carbon tetrachloride, etc.), aprotic polar solvents (e.g. DMF, DMSO, HMPA, etc.), and a mixture thereof. The basic compound includes inorganic bases (e.g. metallic sodium, metallic potassium, metallic magnesium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, etc.), organic bases (e.g. pyridine, piperidine, quinoline, triethylamine, N,N-dimethylaniline, etc.), and the like. The reaction is usually carried out at a temperature of from $0°$ to $120°$ C., preferably from room temperature to $100°$ C., for 0.1 to 5 hours. The phenylsulfonyl halide which may have a lower alkyl substituent on the phenyl ring is usually used in an amount of at least 1 mole, preferably 1 to 3 moles, per 1 mole of the compound [46].

Among the above compounds [3], [5], [7], [9], [10], [1a], [1b], 1b'], [29], [31] and [32], the compounds wherein $R^2$ is a piperidinyl group having oxo group can be converted into the compounds wherein $R^2$ is a piperidinyl group having hydroxy group, by reducing the former compounds. The reduction can be carried out in a suitable solvent in the presence of a reducing agent for hydrogenation. The reducing agent includes, for example, sodium borohydride, lithium aluminum hydride, diborane, and the like, and is usually used in an amount of at least 1 mole, preferably 1 to 5 moles, per 1 mole of the starting material to be reduced. The solvent includes, for example, water, (lower) alcohols (e.g. methanol, ethanol, isopropanol, etc.), ethers (e.g. tetrahydrofuran, diethyl ether, diglyme, etc.), and the like. The reaction is usually carried out at a temperature of from $-60°$ to $50°$ C., preferably from $-30°$ C. to room temperature, for 10 minutes to 5 hours. In case of using lithium alminum hydride or diborane as the reducing agent, it is preferred to employ an anhydrous solvent such as diethyl ether, tetrahydrofuran, diglyme. In case of using sodium borohydride as the reducing agent, an inorganic base such as sodium hydroxide may also be added in the reaction mixture.

The compounds [46], [47] and [48] wherein $R^{35}$ is hydrogen atom can be converted into the corresponding compounds wherein $R^{35}$ is nitro by the same nitration reaction of the compound [44].

The compounds [44] and [45] can be prepared by the process as shown in the following reaction scheme.

[Reaction scheme-XIV]

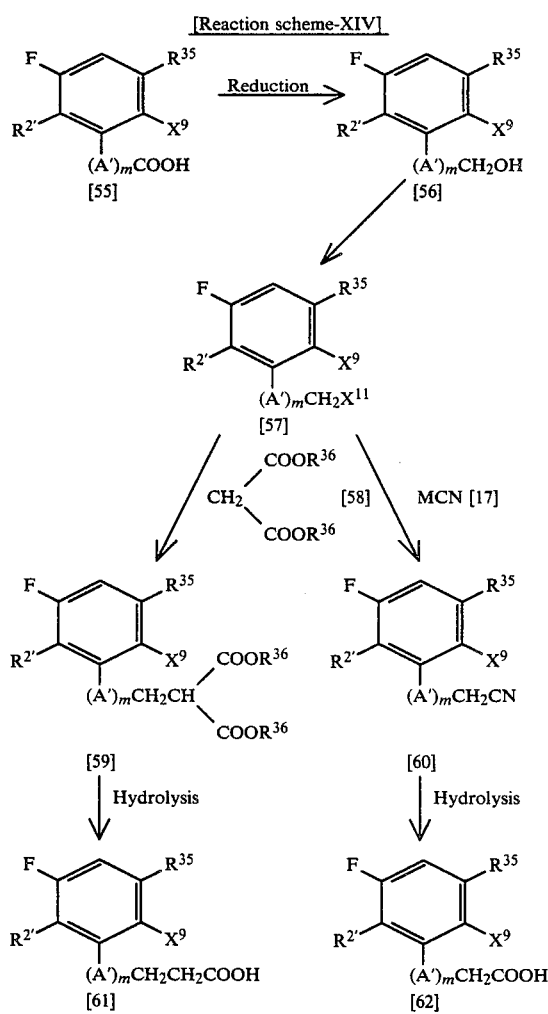

wherein $R^{2'}$, $R^{35}$, $X^9$, M and m are as defined above, and A' is a lower alkylene, provided that the groups $(A')_mCH_2$— and $(A')_mCH_2CH_2$— have not more than 6 carbon atoms, $R^{36}$ is a lower alkyl, and $X^{11}$ is a halogen atom.

The reduction of the compound [55] is carried out under the same conditions as in the reduction of the compound [44] or [45]. Besides, the halogenation of the compound [56] can be carried out under the same conditions as in the halogenation of the compound [46].

The reaction of the compound [57] and the compound [58] is usually carried out in an appropriate solvent in the presence of a basic compound at a temperature of from room temperature to 200° C., preferably from 60 to 120° C., for 1 to 24 hours. The solvent includes, for example, ethers (e.g. dioxane, tetrahydrofuran, ethylene glycol dimethyl ether, diethyl ether, etc.), aromatic hydrocarbons (e.g. benzene, toluene, xylene, etc.), lower alcohols (e.g. methanol, ethanol, isopropanol, etc.), polar solvents (e.g. dimethylformamide, dimethylsulfoxide, etc.), and the like. The basic compound includes, for example, inorganic bases (e.g. calcium carbonate, sodium carbonate, potassium carbonate, sodium hydrogen carbonate, sodium hydroxide, potassium hydroxide, sodium amide, sodium hydride, potassium hydride, sodium methylate, sodium ethylate, etc.), amines (e.g. triethylamine, tripropylamine, pyridine, quinoline, etc.), and the like. The reaction proceeds favorably by using an alkali metal iodide (e.g. potassium iodide, sodium iodide, etc.). The compound [58] is usually used in an equimolar to excess amount, preferably 1 to 5 moles, more preferably 1 to 1.2 mole, per 1 mole of the compound [57].

The reaction of the compound [57] and the compound [17] can be carried out under the same conditions as in the reaction of the compound [16] and the compound [17]. Besides, the hydrolysis of the compound [59] or [60] can be carried out under the same conditions as in the hydrolysis of the compound [20].

The compounds [10] in the reaction scheme-I and the compounds [1b] and [1b'] in the reaction scheme-II are useful not only as an intermediate for preparing the present compounds [1] having antimicrobial activities, but also as an antimicrobial agent because they also have antimicrobial activities.

In the compounds of the present invention there are optical and geometrical isomers, and the present invention includes also these isomers.

Among the present compounds [1], the preferable ones are the compounds wherein $R^3$ is methyl or ethyl (in particular, methyl).

The compounds [1] can easily be converted into a salt thereof by treaing them with a pharmaceutically acceptable acid or base. The acid includes inorganic acids (e.g. hydrochloric acid, sulfuric acid, phosphoric acid, hydrobromic acid, etc.) and organic acids (e.g. oxalic acid, maleic acid, fumaric acid, malic acid, tartaric acid, citric acid, lactic acid, benzoic acid, methanesulfonic acid, propionic acid, etc.). The base includes sodium hydroxide, potassium hydroxide, calcium hydroxide, sodium carboante, potasium hydrogen carbonate, and the like.

The compound thus obtained can easily be isolated by conventional methods, such as extraction with solvents, dilution method, recrystallization, column chromatography, preparative thin layer chromatography, and the like.

The compounds [1] of the present invention or salts thereof show excellent antimicrobial activity against Pseudomonas aeruginosa, anaerobic bacteria, resistant cells against various antimicrobials, clinically isolated bacteria, and gram negative and gram positive bacteria (e.g. Enterococcus faecalis, Staphylococcus pyogenes, etc.), and hence, are useful as an antimicrobial agent for the treatment of diseases induced by these microorganisms. These compounds show also low toxicity and less side effect and are characteristic in good absorbability and in sustained activity. Moreover, the compounds are highly excreted via urine and hence are useful for the treatment of urinary infectious diseases, and further because of easy excretion via bile, they are also useful for the treatment of intestinal infectious diseases. Besides, the compounds of this invention show improved absorbability into body by using them in the form of a salt such as lactate, hydrochloride, etc.

The compounds of the present invention are usually used in the form of a usual pharmaceutical preparation. The pharmaceutical preparation can be prepared in admixture with conventional pharmaceutically acceptable diluents or carriers, such as fillers, weighting agents, binding agents, wetting agents, disintegrators, surfactants, lubricating agents, and the like. The pharmaceutical preparation includes various preparations suitable for treatment of the diseases, for example, tablets, pills, powders, solutions, suspensions, emulsions, granules, capsules, suppositories, injections (solutions, suspensions, etc.), and the like. In the preparation of tablets, there may be used any conventional carriers, for example, excepients (e.g. lactose, white sugar, sodium chloride, glucose, urea, starches, calcium carbonate, kaolin, crystalline cellulose, silicate, etc.), binding agents (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium salts, sodium laurylsulfate, etc.), wetting agents (e.g. glycerin, starches, etc.), adsorbents (e.g. starches, lactose, kaolin, bentonite, colloidal silicates, etc.), rublicants (e.g. purified talc, stearates, boric acid powder, polyethylene glycol, etc.), and the like. The tablets may also be coated with conventional coating agents, for example, may be in the form of a sugar coated tablet, a gelatin-coated tablets, an enteric coating tablet, a film coating tablet, or a double or multiple layers tablet. In the preparation of pills, there may be used conventional carriers, such as excipients (e.g. glucose, lactose, starches, cacao butter, hydrogenated vegetable oils, kaolin, talc, etc.), binding agents (e.g. gum arabic powder, tragacanth powder, gelatin, ethanol, etc.), disintegrators (e.g. laminaran, agar, etc.), and the like. In the preparation of suppositories, there may be used conventional carriers, such as polyethylene glycol, cacao butter, higher alcohols, higher alcohol esters, gelatin, semisynthetized glycerides, and the like. In the preparation of injections, the solutions, emulsions or suspensions of the compounds are sterilized and are preferably made isotonic with the body liquid. These solutions, emulsions and suspensions are prepared by admixing the active compound with a conventional diluent, such as water, aqueous lactic acid solution, ethyl alcohol, propylene glycol, ethoxylated isostearyl alcohol, polyoxylated isostearyl alcohol, polyoxyethylene sorbitan fatty acid esters, and the like. The preparations may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, preservatives, perfumes, flavors, sweeting agents, and other medicaments. The preparations in the form of a paste, cream or gel may be prepared by using as a diluent white vaseline, paraffin, glycerin, cellulose derivatives, polyethylene glycol, silicone, bentonite, or the like.

The pharmaceutical preparation of the present invention may also be in the form of an infusable or injectable solution containing the above compound [1] or a salt thereof (e.g. lactate, etc.), and an acid not producing a precipitate. The acid not producing a precipitate includes, for example, lactic acid, methanesulfonic acid, propionic acid, hydrochloric acid, succinic acid, and the like, preferably lactic acid. In case of using lactic acid, the acid is usually used in an amount of from 0.1 to 10% by weight, preferably from 0.5 to 2% by weight, based on the weight of the above infusable or injectable solution. In case of using an acid other than lactic acid, the acid is usually used in an amount of from 0.05 to 4% by weight, preferably from 0.3 to 2% by weight, based on the weight of the above solution. Moreover, a conventional additive may optionally be added to the above infusable or injectable solution. The additive includes, for example, a thickener, an absorption promoter or inhibitor, a crystallization inhibitor, a complex-forming agent, an antioxidant, an isotonicity-giving agent, or a hydrating agent, and the like. The pH of the solution can properly be adjusted by adding an alkali such as sodium hydroxide, and is usually adjusted within the range of from 2.5 to 7. The infusable or injectable solution thus prepared has an excellent stability, and can be stored and preserved for a long time with retaining the solution state.

The active compounds [1] or salts thereof may be contained in any amount in the preparations, and are usually contained in an amount of 1 to 70% by weight based on the whole weight of the preparations.

The pharmaceutical preparations of the present invention can be administered in any methods. Suitable method for administration may be selected in accordance with the preparation form, age and sex of the patients, degree of severity of the diseases, and the like. For instance, tablets, pills, solutions, suspensions, emulsions, granules and capsules are administered in oral route. In case of injection, it is administered intravenously alone or together with an auxiliary liquid (e.g. glucose, amino acid solution, etc.). The injections may also be administered in intramuscular, intracutaneous, subcutaneous, or intraperitoneal route. Suppositories are administered in intrarectal route.

The dosage of the pharmaceutical preparations of the present invention may vary according to administration methods, age and sex of the patients, severity of the diseases, and the like, but is usually in the range of about 0.2 to 100 mg of the active compound [1] or a salt thereof per 1 kg of body weight of the patient per day. The preparation is usually administered by dividing into 2 to 4 times per day.

The present invention is illustrated by the following Reference Examples, Examples, Preparations, and Experiments.

REFERENCE EXAMPLE 1

To a solution of 2-bromo-4,5-difluoroaniline (100 g) and dimethyl sulfide (49 ml) in anhydrous dichloromethane (1.2 liter) is added gradually N-chlorosuccinimide (90 g) at below 15° C., and thereafter is further added in portions triethylamine (93 ml) at 15° C. After the addition, the mixture is refluxed for 7 hours. After cooling, 10% aqueous sodium hydroxide (one liter) is added to the reaction mixture, and the mixture is extracted with dichloromethane. The extract is dried over magnesium sulfate and concentrated, and the resulting residue is purified by silica gel column chromatography (solvent, dichloromethane:n-hexane=1:2). The product is recrystallized from n-hexane to give 6-bromo-3,4-difluoro-2-methylthiomethylaniline (52 g) as a white crystal, m.p. 60°–61° C.

REFERENCE EXAMPLE 2

A mixture of 6-bromo-3,4-difluoro-2-methylthiomethylaniline (99 g), HMPA (130 g) and copper cyanide (48 g) is heated at 150° C. for 4 hours. After cooling, the reaction mixture is poured into a solution of ethylenediamine (50 ml) in water (500 ml), and the mixture is heated at 60° C. for one hour. After cooling, the mixture is extracted with ethyl acetate, and the extract is dried over magnesium sulfate and concentrated. The resulting residue is purified by silica gel column chromatography (solvent, dichloromethane:n-hexane=1:1), and the product is recrystallized from ethanol to give 2-amino-4,5-difluoro-3-methylthiomethylbenzonitrile (28 g), as a white crystal, m.p. 109°–110° C.

REFERENCE EXAMPLE 3

To a solution of 2-amino-4,5-difluoro-3-methylthiomethylbenzonitrile (4.0 g) in ethanol (80 ml) are added Raney nickel (40 ml) with ethanol (80 ml). The mixture is stirred at 40°–50° C. for 30 minutes, and then filtered. To the filtrate is added water, the reaction mixture is extracted with ethyl acetate. The extract is dried over magnesium sulfate and concentrated. The product is recrystallized from n-hexane to give 2-amino-4,5-difluoro-3-methylbenzonitrile (2.4 g), as a white crystal, m.p. 114°–116° C.

REFERENCE EXAMPLE 4

Sodium nitrite (5.6 g) is added to conc. sulfuric acid (59 ml) at below 70° C. The mixture is heated at 70° C. for 10 minutes and then cooled, and thereto is added dropwise a solution of 2-amino-4,5-difluoro-3-methylbenzonitrile (12.3 g) in acetic acid (123 ml) at below 40° C. The mixture is stirred at the same temperature for 30 minutes and then added in portions to a solution of cuprous chloride (20 g) in conc. hydrochloric acid (200 ml), and thereafter is heated at 80° C. for 30 minutes. After cooling, to the reaction mixture is added ice water, and ethyl acetate is distilled off. The resulting residue is purified by silica gel column chromatography (solvent, dichloromethane:n-hexane=1:1) to give 2-chloro-4,5-difluoro-3-methylbenzonitrile (8.0 g), as a white crystal, m.p. 59°–61° C.

REFERENCE EXAMPLE 5

To 2-chloro-4,5-difluoro-3-methylbenzonitrile (4.0 g) is added 60% sulfuric acid (20 ml), and the mixture is heated at 140°–150° C. for 3 hours. After cooling, the reaction mixture is poured into ice water, and the mixture is extracted with dichloromethane. The extract is dried over magnesium sulfate and the solvent is distilled off. To the residue is added n-hexane, and the precipitate is separated by filtration to give 2-chloro-4,5-difluoro-3-methylbenzoic acid (3.1 g), as a white crystal, m.p. 121°–122° C.

REFERENCE EXAMPLE 6

To 2-chloro-4,5-difluoro-3-methylbenzoic acid (3.1 g) is added thionyl chloride (6 ml), and the mixture is refluxed for one hour. The mixture is concentrated under reduced pressure to give 2-chloro-4,5-difluoro-3-methylbenzoyl chloride (3.3 g).

Separately, metallic magnesium (0.38 g) is suspended in anhydrous ethanol (0.8 ml) and thereto is added a few drops in carbon tetrachloride. When the reaction is started, a mixture of diethyl malonate (2.3 ml), anhydorus ethanol (1.5 ml) and anhydrous toluene (6 ml) is added portionwise at 50°–60° C. Thereto is added dropwise a solution of the above 2-chloro-4,5-difluoro-3-methylbenzoyl chloride (3.3 g) in anhydrous toluene (5 ml) at 0° C. After the addition, the mixture is stirred at room temperature for 30 minutes. To the raction mixture is added a mixture of conc. sulfuric acid (0.4 ml) and water (8 ml) and the mixture is extracted with diethyl ether. The extract is dried over magnesium sulfate and the solvent is then distilled off to give diethyl 2-chloro-3-methyl-4,5-difluorobenzoylmalonate (5.1 g).

REFERENCE EXAMPLE 7

To diethyl 2-chloro-3-methyl-4,5-difluorobenzoylmalonate (5.1 g) are added water (10 ml) and p-toluenesulfonic acid (30 ml), and the mixture is refluxed for 4 hours. After cooling, the mixture is extracted with diethyl ether and the extract is dried over magnesium sulfuate. The diethyl ether is distilled off to give ethyl 2-chloro-4,5-difluoro-3-methylbenzoyl acetate (3.9 g).

REFERENCE EXAMPLE 8

To ethyl 2-chloro-4,5-difluoro-3-methylbenzoylacetate (3.9 g) are added triethoxymethane (3.1 g) and acetic anhydride (3.4 g), and the mixture is heated at 150° C. for one hour. The mixture is concentrated to give ethyl 2-(2-chloro-3-methyl-4,5-difluorobenzoyl)-3-ethoxyacrylate. To the product is added ethanol (50 ml) and thereto is added cyclopropylamine (1.1 ml) at room temperature, and the mixture is stirred for 30 minutes. Ethanol is distilled off to give ethyl 2-(2-chloro-3-methyl-4,5-difluorobenzoyl)-3-cyclopropylaminoacrylate.

To the product is added anhydrous dioxane (30 ml) and thereto is added portionwise 60% sodium hydride (0.6 g). The mixture is stirred at room temperature for 30 minutes and then refluxed for one hour. The reaction mixture is poured into aquoeus saturated ammonium chloride and extracted with dichloromethane. The extract is dried over magnesium sulfate and concentrated to give ethyl 1-cyclopropyl-6,7-difluoro-8-methyl-1,4-dihydro-4-oxoquinoline-3carboxylate (2.2 g).

NMR (CDCl$_3$) δ: 8.64 (1H, s), 8.10 (1H, t, J=10 Hz), 4.36 (2H, q, J=7.5 Hz), 3.76–4.10 (1H, m), 2.76 (3H, d, J=4.5 Hz), 1.37 (3H, t, J=7.5 Hz), 0.86–1.30 (4H, m).

REFERENCE EXAMPLE 9

To ethyl 1-cyclopropyl-6,7-difluoro-8-methyl-1,4-dihydro-4-oxoquinoline-3-carboxylate (2.2 g) are added conc. hydrochloric acid (5 ml), water (2 ml) and acetic acid (20 ml), and the mixture is refluxed for 2 hours. After cooling, the precipitated crystals are separated by filtration, and washed with water, ethanol diethyl ether in this order to give 1-cyclopropyl-6,7-difluoro-8-methyl-1,4-dihydro-4-oxoquinoline-3-carboxylic acid (1.8 g) as a white crystal, m.p. 240°–243° C.

REFERENCE EXAMPLE 10

To 1-cyclopropyl-6,7-difluoro-8-methyl-1,4-dihydro-4-oxoquinoline-3-carboxylic acid (1.0 g) are added triacetylborone [B(OCOCH$_3$)$_3$] (1.0 g) and acetic anhydride (10 ml) and the mixture is heated at 140° C. for 15 minutes. After the reaction, the mixture is concentrated and to the resulting residue is added diethyl ether and the crystals are separated by filtration to give 6,7-difluoro-1-cyclopropyl-8-methyl-1,4-dihydro-4-oxoquinoline-3-carboxylic acid-B(OCOCH$_3$)$_2$ chelate (1.2 g).

NMR (CDCl$_3$) δ: 9.32 (1H, s), 8.23 (1H, t, J=9 Hz), 4.30–4.58 (1H, m), 2.97 (3H, d, J=3 Hz), 2.03 (6H, s), 1.13–1.60 (4H, m).

REFERENCE EXAMPLE 16

Into a solution of 6-bromo-3,4-difluoro-2-methylthiomethylaniline (6.00 g) in ethanol (120 ml) is suspensed Raney nickel (70 ml), and the mixture is stirred at 50° C. for 30 minutes. After removing Raney nickel by filtration, the filtrate is concentrated to give 3,4-difluoro-2-methylaniline (3.77 g) as a colorless oil.

NMR (CDCl$_3$) δ: 6.72 (1H, ddd, J=10.2 Hz, 10.2 Hz, 8.7 Hz), 6.27 (1H, ddd, J=10.2 Hz, 6.0 Hz, 2.7 Hz), 3.43 (2H, br), 2.02 (3H, d, J=2.4 Hz).

REFERENCE EXAMPLE 17

To 3,4-difluoro-2-methylaniline (3.27 g) is added acetic anhydride (50 ml), and the mixture is sirred for 10 minutes. After distilling off acetic anhydride, the resulting residue is extracted with dichloromethane. The extract is washed with water, aqueous saturated sodium hydrogen carbonate and aqueous saturated sodium chloride in this order, and then dried over anhydrous magnesium sulfate. After distilling off dichloromethane, the residue is recrystallized from ethyl acetate-n-hexane to give 3,4-difluoro-2-methylacetanilide (3.86 g) as colorless needles, m.p. 145.5°–146.0° C.

REFERENCE EXAMPLE 18

3,4-Difluoro-2-methylacetanilide (100 mg) is added to ice-cooled conc. sulfuric acid (0.3 ml) and thereto is added conc. nitric acid (0.1 ml) under ice cooling, and the mixture is stirred at room temperature for 2 hours. To the mixture is further added conc. nitric acid (0.1 ml), and the mixture is stirred at room temperature overnight. To the reaction mixture is added a large amount of water, and the mixture is extracted with dichloromethane. The extract is washed with water, aqueous saturated sodium hydrogen carbonate and aqueous saturated sodium chloride in this order and then dried over anhydrous magnesium sulfate. After distilling off dichloromethane, the residue is recrystallized from ethyl acetate-n-hexane to give 4,5-difluoro-6-methyl-2-nitroacetanilide (80.7 mg) as yellow needles, m.p. 152.1°–152.6° C.

REFERENCE EXAMPLE 19

4,5-Difluoro-6-methyl-2-nitroacetanilide (81 mg) is dissolved in acetic acid (2 ml) and thereto is added conc. hydrochloric acid (1 ml) at 0° C. The mixture is stirred at 100° C. overnight and then concentrated. The residue is neutralized with aqueous saturated sodium hydrogen carbonate and extracted with dichloromethane. The extract is washed with aqueous saturated sodium chloride and dried over anhydrous magnesium sulfate. Dichloromethane is distilled off to give 4,5-difluoro-6-methyl-2-nitroaniline (59 mg) as orange prisms, m.p. 87.2°–88.0° C.

REFERENCE EXAMPLE 20

Sodium nitrite (30 mg) is added portionwise to conc. hydrochloric acid (0.32 ml), and the mixture is stirred at 70° C. for 10 minutes and cooled to room temperature and thereto is added dropwise a solution of 4,5-difluoro-6-methyl-2-nitroanline (59 mg) in acetic acid (6.5 ml) at the same temperature. The mixture is stirred at room temperature for 30 minutes and thereto is added dropwise a solution of cuprous chloride (107 mg) in conc. hydrochloric acid (1.0 ml). The mixture is stirred at 80° C. for 30 minutes. To the reaction mixture is added water and the mixture is extracted with ethyl acetate. The extract is washed with water, aqueous saturated sodium hydrogen caronate and aqueous saturated sodium chloride in this order and then dried over anhydrous magnesium sulfate. Ethyl acetate is distilled off to give 2-chloro-5,6-difluoro-3-nitrotoluene (54 mg).

NMR (CDCl$_3$) δ: 7.58 (1H, dd, J=11.0 Hz, 8.0 Hz), 2.40 (3H,s).

REFERENCE EXAMPLE 23

To a solution of 3,4-difluoroacetanilide (85.5 g) in sulfuric acid (850 ml) is added gradually with stirring potassium nitrate (55.5 g) at room temperature during which the temperature raises to 60° C. The mixture is stirred at 60° C. for one hour. The reaction mixture is poured into ice water, and the precipitated crystals are taken by filtration. The precipitates are dissolved in dichloromethane and washed with aqueous sodium hydrogen carbonate, water and aqueous saturated sodium chloride in this order and dried. The solvent is removed by concentration and washed with n-hexane. The resulting crystals are taken by filtration and dried to give 2-nitro-4,5-difluoroaniline (54 g.).

NMR (CDCl$_3$) δ: 5.76–6.40 (2H, m), 6.60 (1H, dd, J=12 Hz, 7 Hz), 7.97 (1H, dd, J=10.5 Hz, 8.5 Hz).

REFERENCE EXAMPLE 24

To a solution of 2-nitro-4,5-difluoroaniline (1.0 g) and dimethylsulfide (1.79 g) in dichloromethane (40 ml) is added gradually N-chlorosuccinimide (3.82 g) with stirring at below 15° C. The mixture is stirred for 30 minutes, and thereto is added triethylamine (2.89 g), and the mixture is refluxed for 21 hours. After allowing to cool, the reaction mixture is washed with 10% aqueous sodium hydroxide, water and aqueous sodium chloride in this order and dried. The solvent is removed by concentration, and the resulting residue is purified by silica gel column chromatography (solvent, n-hexane:ethylacetate=30:1) and then recrystallized from n-nexane to give 2-nitro-4,5-difluoro-6-methylthiomethylaniline (0.47 g) as yellow needles, m.p. 110°–111.5° C.

REFERENCE EXAMPLE 25

Sodium nitrite (0.15 g) is added to conc. sulfuric acid (15 ml) and the mixture is stirred at 70° C. for 10 minutes. To the mixture is added dropwise a solution of 2-nitro-4,5-difluoro-6-methylthiomethylaniline (0.45 g) in acetic acid (4.5 ml). The mixture is stirred at the same temperature for 45 minutes, and thereto is further added dropwise a solution of cuprous chloride (0.52 g) in conc. hydrochloric acid (5.2 ml). The mixture is stirred at 80° C. for 1.5 hour, and the reaction mixture is poured into ice water and extracted with ethyl acetate. The extract is washed with water and aqueous saturated sodium chloride in this order and dried, and then the solvent is disilled off. The resulting residue is purified by silica gel column chromatography (solvent, n-hexane:ethyl acetate=30:1) to give 2-chloro-3-methylthio-4,5-difluoro-1-nitrobenzene (0.16 g).

NMR (CDCl$_3$) δ: 2.15 (3H, s), 3.92 (2H, dd, J=3 Hz), 7.67 (1H, dd, J=8.5 Hz, 8 Hz)

REFERENCE EXAMPLE 26

2,3,6-Trifluorobenzoic acid (21.0 g) is added to conc. sulfuric acid (120 ml) under ice-cooling. To the mixture is added dropwise a solution of potassium nitrate (14.5 g) in conc sulfuric acid (30 ml) at below 20° C. After the addition, the mixture is stirred at room temperature for one hour. The reaction mixture is poured into ice water and extracted with diethyl ether. The extract is dried over magnesium sulfate, and then the solvent is distilled off. The residue is recrystallized from dichloromethane-n-hexane to give 2,5,6-trifluoro-3-nitrobenzoic acid (22 g), as colorless prisms, m.p. 98°–99° C.

NMR (CDCl$_3$) δ: 8.11–8.23 (1H, m), 9.10 (1H, brs).

REFERENCE EXAMPLE 27

To a solution of sodium boron hydroxide (44 g) in anhydrous tetrahydrofuran is added a solution of 2,5,6-trifluoro-3-nitrobenzoic acid (22 g) in anhydrous tetrahydrofuran (40 ml) at below 10° C., and thereto is further added dropwise a solution of boron trifluoride etherate (20 ml) in anhydrous tetrahydrofuran (40 ml) at below 10° C. After the addition, the mixture is stirred at room temperature for one hour. The reaction mixture is poured into ice water and extracted with diethyl ether. The extract is dried, and then the solvent is distilled off to give 2,5,6-trifluoro-3-nitrobenzyl alcohol (14 g).

NMR (CDCl$_3$) δ: 2.56 (1H, brs), 4.88 (2H, t, J=1.8 Hz), 7.92–8.04 (1H, m)

REFERENCE EXAMPLE 28

To a solution of 2,5,6-trifluoro-3-nitrobenzyl alcohol (14 g) in ethanol (64 ml) and water (7 ml) is added a mixture of 4-ethoxycarbonylpiperazine (11 g), triethylamine (12.5 g) and ethanol (18 ml) at one time. The mixture is stirred at room temperature overnight, and the resulting precipitates are separated by filtration. The crystals are washed with a small amount of diethyl ether and recrystallized from ethanol to give 3,6-difluoro-2-(4-ethoxycarbonyl-1-piperazinyl)-5-nitrobenzyl alcohol (8.7 g), as yellow needles, m.p. 147°–149° C.

REFERENCE EXAMPLE 29

To a solution of 3,6-difluoro-2-(4-ethoxycarbonyl-1-piperazinyl)-5-nitrobenzyl alcohol (8.5 g) in chloroform (85 ml) is added thionyl chloride (2.7 ml) at room temperature. The mixture is stirred at the same temperature for 30 minutes, and the reaction mixture is poured into ice water, and then neutralized with sodium hydrogen carbonate and extracted with diethyl ether. The extract is dried over magnesium sulfate, and then the solvent is distilled off to give 2-(4-ethoxycarbonyl-1-piperazinyl)-3,6-difluoro-5-nitorbenzyl chloride (8.1 g).

NMR (CDCl$_3$) δ: 1.28 (3H, t, J=7.1 Hz), 3.08–3.33 (4H, m), 3.46–3.75 (4H, m), 4.18 (2H, q, J=7.1 Hz), 4.77 (2H, d, J=2.5 Hz), 7.82 (1H, dd, J=9.2 Hz, 7.2 Hz).

REFERENCE EXAMPLE 30

To a solution of 3,6-difluoro-2-(4-ethoxycarbonyl-1-piperazinyl)-5-nitrobenzyl chloride (8.1 g) in dimethylsulfoxide (90 ml) is added gradually sodium boron hydride (1.8 g) at below 30° C. The mixture is stirred at the same temperature for one hour, and the reaction mixture is poured into ice water, and then acidified with conc. hydrochloric acid and extracted with diethyl ether. The solvent is distilled off to give 2-(4-ethoxycarbonyl-1-piperazinyl)-3,6-difluoro-5-nitrotoluene (7.1 g).

NMR (CDCl$_3$) δ: 1.26 (3H, t, J=7.1 Hz), 2.30 (3H, d, J=3 Hz), 2.76–3.27 (5H, m), 3.50–3.75 (4H, m), 4.17 (2H, q, J=7.1 Hz), 7.60 (1H, dd, J=9.3 Hz, 7.2 Hz).

REFERENCE EXAMPLE 31

To 3,6-difluoro-2-(4-ethoxycarbonyl-1-piperazinyl)-5-nitrotoluene(7.1 g) are added anhydrous dimethylsulfoxide (23 ml), potassium fluoride (2.0 g) and cyclopropylamine (1.5 g), and the mixture is heated at 60° C. for 6 hours. The reaction mixture is poured into ice water, and extracted with dichloromethane. The solvent is distilled off and the residue is recrystallized from ethanol to give N-cyclopropyl-2-methyl-3-(4-ethoxycarbonyl-1-piperazinyl)-4-fluoro-6-nitroaniline (7.4 g), as orange red prisms, m.p. 97°–98° C.

NMR (CDCl$_3$) δ: 0.50–0.54 (2H, m), 0.66–0.74 (2H, m), 1.28 (3H, t, J=7.1 Hz), 2.43 (3H, s), 2.63–2.90 (1H, m), 3.07–3.28 (4H, m), 3.47–3.77 (4H, m), 4.20 (2H, q, J=7.1 Hz), 7.53 (1H, brs), 7.70 (1H, dd, J=Hz).

REFERENCE EXAMPLE 32

To N-cyclopropyl-2-methyl-3-(4-ethoxycarbonyl-1-piperazinyl)-4-fluoro-6-nitroaniline (7.1 g) is added diethyl ethoxymethylenemalonate (4.6 g), and the mixture is reacted at 150°–170° C. for 17 hours. After cooling, the solvent is distilled off, and the resulting residue is subjected to silica gel column chromatography (solvent, dichloromethane:n-hexane=2:1→dichloromethane) to give diethyl [N-cyclopropyl-N-[3-(4-ethoxycarbonyl-1-piperazinyl)-2-methyl-4-fluoro-6-nitrophenyl]aminomethylene]malonate (5.4 g).

REFERENCE EXAMPLE 33

To a solution of diethyl [N-cyclopropyl-N-[3-(4-ethoxycarbonyl-1-piperazinyl)-2-methyl-4-fluoro-6-nitrophenyl]aminomethylene]malonate (1.0 g) in acetic anhydride (5 ml) is added conc. sulfuric acid (2 ml) with keeping at 50°–70° C. After stirring for 30 minutes, the reaction mixture is poured into ice water, and neutralized with potassium carbonate. The mixture is extracted with ethyl acetate, and the solvent is distilled off, and the resulting residue is purified by silica gel column chromatography (solvent, dichloromethane:methanol=10:1) and then recrystallized from ethyl acetate to give ethyl 1-cyclopropyl-7-(4-ethoxycarbonyl-1-peperazinyl)-6-fluoro-8-methyl-1,4-dihydro-4-oxoquinoline-3-carboxylate (0.19 g), as colorless prisms, m.p. 200°–202° C.

In the same manner as described in Reference Example 33 by using appropriate starting materials, there are prepared the same compounds as in Reference Example 8.

REFERENCE EXAMPLES 39

In the same manner as described in Reference Example 28 by using appropriate starting material, there is prepared the following compound:

3,6-Difluoro-2-(3-amino-1-pyrrolidinyl)-5-nitrobenzyl alcohol, m.p. 117.0°–118.5° C., orange prisms (recrystallized from ethyl acetate-n-hexane).

REFERENCE EXAMPLE 40

To 3,6-difluoro-2-(3-amino-1-pyrrolidinyl)-5-nitrobenzyl alcohol (43 mg) is added acetic anhydride (0.5 ml) at room temperature. The mixture is stirred at the same temperature for 10 minutes, and the reaction mixture is diluted with water and extracted with dichloromethane. The organic layer is washed with water and aqueous saturated sodium chloride in this order and dried over anhydrous magnesium sulfate, and then solvent is distilled off. The resulting residue is purified by silica gel column chromatography (solvent, dichloromethane→methanol:dichloromethane=1:12) and then recrystallized from dichloromethane to give 2-(3-acetylamino-1-pyrrolidinyl)-3,6-difluoro-5-nitrobenzyl alcohol (40 mg), as yellow prisms, m.p. 142.5°–143.5° C.

REFERENCE EXAMPLES 41

In the same manner as described in Reference Example 29 by using appropriate starting material, there is prepared the following compound:

2-(4-Acetylamino-1-pyrrolidinyl)-3,6-difluoro-5-nitrobenzyl chloride.

NMR (CDCl$_3$) δ: 7.74 (1H, dd, J=12.0 Hz, 7.5 Hz), 6.16 (1H, d, J=5.4 Hz), 4.78 (1H, dd, J=11.3 Hz, 3.0 Hz), 4.69 (1H, dd, J=11.3 Hz, 3.0 Hz), 4.62–4.50 (1H, m), 3.97–3.69 (2H, m), 3.67–3.50 (1H, m), 3.49–3.32 (1H, m), 2.40–2.18 (1H, m), 2.12–1.93 (1H, m), 1.98 (3H, s)

REFERENCE EXAMPLES 42

In the same manner as described in Reference Example 30 by using appropriate starting material, there is prepared the following compound:

2-(3-Acetylamino-1-pyrrolidinyl)-3,6-difluoro-5-nitrotoluene, m.p. 139.0°–140.3° C., yellow needles (recrystallized from dichloromethane).

REFERENCE EXAMPLES 43

In the same manner as described in Reference Example 31 by using appropriate starting material, there is prepared the following compound:

N-Cyclopropyl-2-methyl-3-(3-acetylamino-1-pyrrolidinyl)-4-fluoro-6-nitroaniline, m.p. 162.5°–164.0° C., orange prisms (recrystallized from ethyl acetate-n-hexane).

REFERENCE EXAMPLES 44

In the same manner as described in Reference Example 32 by using appropriate starting material, there is prepared the following compound:

Diethyl [N-cyclopropyl-N-[3-(3- acetylamino-1-pyrrolidinyl)-4-fluoro-2-methyl-6-nitrophenyl]aminomethylene]malonate NMR (CDCl$_3$) δ: 7.73 (1H, s), 7.68 (1H, d, J=11.6 Hz), 5.97 (1H, br), 4.62–4.45 (1H, m), 4.12 (4H, q, J=7.2 Hz), 3.85–3.15 (5H, m), 2.42–1.95 (5H, m), 1.98 (3H, s), 1.29 (6H, t, J=7.2 Hz), 0.93–0.52 (4H, m).

REFERENCE EXAMPLES 45

In the same manner as described in Reference Example 33 by using appropriate starting material, there is prepared the following compound:

Ethyl 1-cyclopropyl-7-(3-acetylamino-1-pyrrolidinyl)-6-fluoro-8-methyl-1,4-dihydro-4-oxoquinoline-3-carboxylate, m.p. 215.5°–217.0° C., white powder (recrystallized from ethanol-ethyl acetate-diethyl ether).

REFERENCE EXAMPLES 54

In the same manner as described in Reference Example 28 by using appropriate starting material, there are prepared the following compounds:

3,6-Difluoro-2-(3-acetamidomethyl-1-pyrrolidinyl)-5-nitrobenzyl alcohol, m.p. 120°–121° C., yellow crysals.

NMR (CDCl$_3$+DMSO-d$_6$) δ: 1.55–1.83 (1H, m), 1.95 (3H, s), 1.99–2.10 (1H, m), 2.39–2.57 (1H, m), 3.14–3.82 (6H, m), 4.72 (2H, d, J=2.6 Hz), 7.31 (1H, brs), 7.70 (1H, dd, J=7.5 Hz, 13.5 Hz).

3,6-Difluoro-2-[3-(N-methyl-N-benzylamino)-1-pyrrolidinyl]-5-nitrobenzyl alcohol.

NMR (CDCl$_3$) δ: 7.75 (1H, dd, J=7.5 Hz, 13.1 Hz), 7.41–7.20 (5H, m), 3.85–3.60 (4H, m), 3.62 (1H, d, J=13.1 Hz), 3.52 (1H, d, J=13.1 Hz), 3.25–3.05 (1H, m), 2.35–1.92 (3H, m), 2.20 (3H, s).

REFERENCE EXAMPLES 55

In the same manner as described in Reference Example 29 by using appropriate starting material, there are prepared the following compounds;

2,5-Difluoro-3-chloromethyl-4-[3-(N-methyl-N-benzylamino)-1-pyrrolidinyl]nitrobenzene.

NMR (CDCl$_3$) δ: 7.78(1H, dd, J=7.6 Hz, 13.4 Hz), 7.42–7.22 (5H, m), 4.78 (1H, dd, J=2.7 Hz, 12.1 Hz), 4.67 (1H, dd, J=2.7 Hz, 12.1 Hz), 3.92–3.55 (4H, m), 3.67 (1H, d, J=13.1 Hz), 3.53 (1H, d, J=13.1 Hz), 3.30–3.10 (1H, m), 2.35–1.88 (2H, m), 2.22 (3H, s).

2,5-Difluoro-3-chloromethyl-4-(3-acetamidomethyl-1-pyrrolidinyl)nitrobenzene, m.p. 94°–98° C., yellow crystal, NMR (CDCl$_3$+DMSO-d$_6$) δ: 1.68–1.90 (1H, m), 2.07 (3H, s), 2.00–2.25 (1H, m), 2.50–2.68 (1H, m), 3.20–3.79 (6H, m), 4.78 (2H, d, J=2.6 Hz), 7.78 (1H, dd, J=7.5 Hz, 13.5 Hz), 8.18 (1H, brs).

REFERENCE EXAMPLE 56

In the same manner as described in Reference Example 30 by using appropriate starting materials, there are prepared the following compounds.

3,6-Difluoro-5-nitro-2-[3-(N-methyl-N-benzylamino)-1-pyrrolidinyl]toluene,

NMR (CDCl$_3$) δ: 7.65 (1H, dd, J=7.1 Hz, 12.8 Hz), 7.38–7.20 (5H, m), 3.79–3.45 (4H, m), 3.62 (1H, d, J=13.4 Hz), 3.50 (1H, d, J=13.4 Hz), 3.30–3.06 (1H, m), 2.35–2.13 (1H, m), 2.25 (3H, d, J=3.2 Hz), 2.20 (3H, s), 2.11–1.88 (1H, m).

3,6-Difluoro-5-nitro-2-(3-acetamidomethyl-1-pyrrolidinyl)-toluene, m.p. 82°–84° C., yellow crystals.

NMR (CDCl$_3$) δ: 1.60–1.78 (1H, m), 2.00 (3H, s), 2.02–2.20 (1H, m), 2.24 (3H, d, J=3.2 Hz), 2.40–2.66 (1H, m), 3.20–3.62 (6H, m), 5.67 (1H, brs), 7.63 (1H, dd, J=7.5 Hz, 13.5 Hz).

REFERENCE EXAMPLES 57

In the same manner as described in Reference Example 31 by using appropriate starting material, there are prepared the following compounds:

N-Cyclopropyl-2-methyl-3-[3-(N-methyl-N-benzylamino)-1-pyrrolidinyl]-4-fluoro-6-nitroaniline.

NMR (CDCl$_3$) δ: 7.87 (1H, s), 7.69 (1H, d, J=11.7 Hz), 7.40–7.22 (5H, m), 3.81–3.41 (4H, m), 3.65 (1H, d, J=10.6 Hz), 3.55 (1H, d, J=10.6 Hz), 3.24–3.08 (1H, m), 2.86–2.72 (1H, m), 2.32–2.10 (1H, m), 2.29 (3H, s), 2.21 (3H, s), 2.08–1.90 (1H, m), 0.88–0.56 (3H, m), 0.51–0.41 (1H, m).

N-Cyclopropyl-2-methyl-3-(3-acetamidomethyl-1-pyrrolidinyl)-4-fluoro-6-nitroaniline.

NMR (CDCl$_3$) δ: 0.40–0.85 (4H, m), 1.60–1.83 (1H, m), 2.01 (3H, s), 2.04–2.20 (1H, m), 2.28 (3H, s), 2.42–2.60 (1H, m), 2.70–2.88 (1H, m), 3.20–3.65 (6H, m), 5.89 (1H, brs), 7.65 (1H, d, J=14.6 Hz), 7.86 (1H, brs).

REFERENCE EXAMPLES 58

In the same manner as described in Reference Example 32 by using appropriate starting material, there is prepared the following compound:

Diethyl [N-Cyclopropyl-N-[3-[3-(N-benzyl-N-methylamino)-1-pyrrolidinyl)]-2-methyl-4-fluoro-6-nitrophenyl]aminomethylene]malonate.

NMR (CDCl$_3$) δ: 7.85–7.60 (2H, m), 7.40–7.16 (5H, m), 4.25–4.06 (2H, m), 3.80–3.05 (8H, m), 2.19 (6H, s), 2.32–1.89 (2H, m), 1.23 (6H, t, J=7.1 Hz), 1.12–0.41 (4H, m).

REFERENCE EXAMPLES 59

In the same manner as described in Reference Example 33 by using appropriate starting material, there are prepared the following compounds:

Ethyl 1-cyclopropyl-7-[3-(N-benzyl-N-methylamino]-1-pyrrolidinyl]-6-fluoro-8-methyl-1,4-dihydro-4-oxoquinoline-3-carboxylate, m.p. 145°–148.5° C. (decomp.) (recrystallized from ethyl acetate-diethyl ether), pale yellow powder.

Ethyl 1-cyclopropyl-7-(3-acetamidomethyl-1-pyrrolidinyl)-6-fluoro-8-methyl-1,4-dihydro-4-oxoquinoline-3-carboxylate, m.p. 208°–210° C. (recrystallized from ethanol), white crystals.

REFERENCE EXAMPLE 66

To 2-chloro-5,6-difluoro-3-nitrotoluene (1.0 g) are added spray-dried potassium fluoride (1.4 g), anhydrous dimethylsulfoxide (10 ml) and benzene (10 ml), and the moisture is removed by azeotropic distillation together with benzene. Subsequently, the mixture is stirred at 170°–180° C. under argon stream for 3.5 hours. After cooling, the reaction mixture is poured into ice water and extracted with diethyl ether. The extract is washed with water, dried and then the solvent is distilled off. The residue is purified by silica gel column chromatography (solvent, n-hexane) to give 2,5,6-trifluoro-3-nitrotoluene (0.45 g).

NMR (CDCl$_3$) δ: 2.34–2.37 (3H, m), 7.75–8.00 (1H, m).

REFERENCE EXAMPLE 67

To a solution of 3-amino-1-benzyl-4-methylpyrrolidine (9.5 g) in methanol (190 ml) is added anhydrous t-butoxycarboxylic acid (13.0 g) at room temperature, and the mixture is stirred for one hour. Methanol is distilled off under reduced pressure, and to the resulting residue is added water. The mixture is extracted with dichloromethane, and the extract is dried over magnesium sulfate and then dichloromethane is distilled off. The residue is purified by silica gel column chromatography (solvent, dichloromethane:methanol=19:1) to give 3-(t-butoxycarbonylamino)-1-benzyl-4-methylpyrrolidine (isomer A) (4.4 g), as colorless prisms, m.p. 131.5°–132.7° C.

NMR (CDCl$_3$) δ: 1.09 (3H, d, J=6.7 Hz), 1.43 (9H, s), 1.86–2.02 (2H, m), 2.62 (2H, d, J=6.1 Hz), 2.93–3.05 (1H, m), 3.56 (2H, s), 3.68 (1H, brs), 4.84 (1H, brs), 7.20–7.37 (5H, m).

REFERENCE EXAMPLES 68

To 3-(t-butoxycarbonylamino)-1-benzyl-4-methylpyrrolidine (3.9 g) are added ethanol (50 ml) and 10% Pd-C (780 mg), and the mixture is subjected to catalytic reduction at 60° C. under atmospheric pressure. After the catalytic reduction, the catalyst is removed off by filtration, and the filtrate is concentrated. The resulting residue is recrystallized from ethyl acetate-petroleum ether to give 3-(t-butoxycarbonylamino)-4-methylpyrrolidine (isomer A) (2.01 g), as colorless prisms, m.p. 86.8°–87° C.

NMR (CDCl$_3$) δ: 1.08 (3H, d, J=6.8 Hz), 1.45 (9H, s), 1.83–1.97 (1H, m), 2.10 (1H, brs), 2.43–2.52 (1H, m), 2.52–2.81 (1H, m), 3.10–3.35 (2H, m), 3.53–3.73 (1H, m), 4.69 (1H, brs).

REFERENCE EXAMPLE 69

To a solution of sodium boron hydride (51.6 g) in tetrahydrofuran (500 ml) is added dropwise a solution of 2,5,6-trifluorobenzoic acid (120 g) in tetrahydrofuran (200 ml) with stirring at below 10° C., and thereto is further added dropwise a solution of BF$_3$·(C$_2$H$_5$)$_2$O (232 ml) in tetrahydrofuran (500 ml) under ice cooling. The mixture is stirred at room temperature overnight. The reaction mixture is poured into ice water (1.5 liter) and is extracted with diethyl ether. The extract is dried over magnesium sulfate and the solvent is distilled off under reduced pressure to give 2,3,6-trifluorobenzyl alcohol (112.7 g), as pale yellow oil, b.p. 112° C. (30 mmHg).

REFERENCE EXAMPLE 70

To a solution of 2,3,6-trifluorobenzyl alcohol (41 g) in dichloromethane (100 ml) is added dropwise a solution of thionyl chloride (50 ml) in dichloromethane (80 ml) under ice cooling with stirring, and the mixture is stirred at room temperature overnight. To the mixture is added triethylamine (10 ml), and the solvent is distilled off under reduced pressure to give 2,3,6-trifluorobenzyl chloride (28.6 g), as colorless oil, b.p. 63° C. (13 mmHg).

NMR (CDCl$_3$) δ: 4.66 (2H, s), 6.62–6.93 (1H, m), 7.04–7.26 (1H, m).

REFERENCE EXAMPLE 71

To a solution of sodium cyanide (1.94 g) in water (4 ml) is added with phenyltriethylammonium chloride (0.09 g), and thereto is added with stirring 2,3,6-trifluorobenzyl chloride (5.0 g), and the mixture is stirred at 90° to 100° C. for 40 minutes. The reaction mixture is poured into water (20 ml) and is extracted with diethyl ether. The extract is dried over potassium carbonate and the solvent is distilled off to give 2-(2,3,6-trifluorophenyl)acetonitrile (3.1 g), b.p. 80°–85° C. (5 mmHg).

NMR (CDCl$_3$) δ: 3.76 (2H, d, J=0.8 Hz), 6.89–6.98 (1H, m), 7.11–7.26 (1H, m).

REFERENCE EXAMPLE 72

2-(2,3,6-Trifluorophenyl)acetonitrile (13.3 g) is dissolved in ethanol (20 ml), and thereto is carefully added conc. sulfuric acid (8.5 ml), and the mixture is refluxed at 125° C. for 7 hours. After cooling, the reaction mixture is fractionated with diethyl ether and water. The ether layer is washed with aqueous saturated sodium chloride and dried over magnesium sulfate and then concentrated under reduced pressure to give ethyl 2-(2,3,6-trifluorophenyl)acetate (16.3 g), as colorless oil.

NMR (CDCl$_3$) δ: 1.27 (3H, t, J=7.1 Hz), 3.72 (2H, d, J=1.2 Hz), 4.19 (2H, q, J=7.1 Hz), 6.78–6.90 (1H, m), 7.00–7.16 (1H, m).

REFERENCE EXAMPLE 73

Ethyl 2-(2,3,6-trifluorophenyl)acetate (16.2 g) is dissolved in ethanol (60 ml). The mixture is stirred and thereto is added 3N sodium hydroxide (200 ml), and the mixture is stirred at 70° C. for one hour. After cooling, 6N hydrochloric acid (120 ml) is added to the mixture. The resulting white powdery precipitates are dissolved by adding thereto diethyl ether. The diethyl ether layer is separated and dried over magnesium sulfate and then concentrated under reduced pressure to give 2-(2,3,6-trifluorophenyl)acetic acid (13.9 g), as white crystals.

NMR (CDCl$_3$) δ: 3.79 (2H, s), 6.79–6.91 (1H, m), 7.02–7.18 (1H, m), 9.75 (1H, s).

REFERENCE EXAMPLE 74

Lithium aluminum hydride (0.8 g) is suspended in dry diethyl ether (5 ml) and the mixture is stirred. To the mixture is added dropwise a solution of 2-(2,3,6-trifluorophenyl)acetic acid (2.0 g) in dry diethyl ether (15 ml), and the mixture is refluxed for 30 minutes. To the reaction mixture are added water (0.8 ml), 10% aqueous sodium hydroxide (0.8 ml) and water (1.6 ml) in this order, and the mixture is stirred at room temperature. To the mixture is added diethyl ether (10 ml), and the resulting precipitates are separated by filtration and washed with tetrahydrofuran. The washing liquid and the filtrate are combined and then concentrated under reduced pressure to give 2-(2,3,6-trifluorophenyl)ethyl alcohol (1.9 g), as colorless oil.

NMR (CDCl$_3$) δ: 1.75 (1H, s), 2.98 (3H, t, J=6.7 Hz), 3.85 (2H, t, J=6.7 Hz), 6.74–6.87 (1H, m), 6.93–7.09 (1H, m).

REFERENCE EXAMPLE 75

To a solution of 2-(2,3,6-trifluorophenyl)ethyl alcohol (1.5 g) in methylene chloride (10 ml) are added with stirring p-toluenesulfonyl chloride (2.2 g) and triethylamine (2.0 ml), and the mixture is stirred at room temperature for 5 hours. The reaction mixture is poured into water and is extracted with diethyl ether. The ether layer is washed with aqueous saturated sodium hydrogen carbonate and aqueous saturated sodium chloride and dried over magnesium sulfate and then concentrated under reduced pressure. The resulting residue is purified by silica gel column chromatography (solvent, methylene chloride) and recrystallized from diethyl ether-n-hexane to give 1-[2-(p-toluenesulfonyloxy)ethyl]-2,3,6-trifluorobenzene (3.4 g), as colorless prisms, m.p. 73°–74° C.

NMR (CDCl$_3$) δ: 2.44 (3H, s), 3.03 (3H, t, J=6.5 Hz), 4.23 (2H, t, J=6.5 Hz), 6.70–6.82 (1H, m), 6.93–7.09 (1H, m), 7.29 (2H, d, J=8.5 Hz), 7.70 (2H, d, J=8.5 Hz).

REFERENCE EXAMPLE 76

Lithium aluminum hydride (5.6 g) is suspended in dry diethyl ether (70 ml) and thereto is added dropwise with stirring a solution of 1-[2-(p-toluenesulfonyloxy)ethyl]-2,3,6-trifluorobenzene (23.3 g) in dry diethyl ether (170 ml) at below 10° C., and the mixture is stirred at room temperature for one hour. To the reaction mixture are added water (5.6 ml), 10% aqueous sodium hydroxide (10.0 ml) and water (5.6 ml) in this order, and the mixture is stirred at room temperature for 30 minutes. The resulting white precipitates are filtered off, and the filtrate is concentrated under atmospheric pressure to give 2,3,6-trifluoro-1-ethylbenzene (13.2 g), as colorless oil.

NMR (CDCl$_3$) δ: 1.22 (3H, t, J=7.1 Hz), 2.72 (2H, q, J=7.1 Hz), 6.71–6.82 (1H, m), 6.87–7.03 (1H, m).

REFERENCE EXAMPLE 77

2,3,6-Trifluoro-1-ethylbenzene (1.09 g) is dissolved in conc. sulfuric acid (5.5 ml), and thereto is added with stirring a mixture of potassium nitrate (0.83 g) in conc. sulfuric acid (4 ml) at room temperature, and the mixture is stirred at the same temperature for one hour. The reaction mixture is poured into cold water (100 ml) and is extracted with diethyl ether. The ether layer is washed with aqueous saturated sodium chloride and dried over magnesium sulfate and then concentrated under reduced pressure to give 3-ethyl-2,4,5-trifluoronitrobenzene (1.14 g), as yellow oil.

NMR (CDCl$_3$) δ: 1.27 (3H, t, J=7.6 Hz), 2.77–2.89 (2H, m), 7.83 (1H, dd, J=8.0 Hz, 16.2 Hz).

REFERENCE EXAMPLE 80

In the same manner as described in Reference Example 67 by using an appropriate starting material, there is prepared the following compound.

3-(t-Butoxycarbonylamino)-1-benzyl-4-methylpyrrolidine (isomer B), colorless needles, m.p. 83°–83.5° C. (recrystallized from n-hexane).

NMR (CDCl$_3$) δ: 0.93 (3H, d, J=6.98 Hz), 1.44 (9H, s), 2.14–2.54 (3H, m), 2.60–2.93 (2H, m), 3.58 (2H, dd, J=13.03 Hz, 14.91 Hz), 4.07–4.31 (1H, m), 4.61–4.82 (1H, m), 7.14–7.39 (5H, m).

REFERENCE EXAMPLE 81

In the same manner as described in Reference Example 68 by using an appropriate starting material, there is prepared the following compound.

3-(t-Butoxycarbonylamino)-4-methylpyrrolidine (isomer B), b.p. 106°–109° C. (0.25 mmHg).

NMR (CDCl$_3$) δ: 0.97 (3H, d, J=6.9 Hz), 1.45 (9H, s), 1.93 (1H, brs), 2.10–2.33 (1H, m), 2.61–2.79 (1H, m), 3.04–3.33 (2H, m), 3.97–4.21 (1H, m), 4.63–4.87 (1H, m).

REFERENCE EXAMPLE 82

In the same manner as described in Reference Example 32 by using an appropriate starting material, there is prepared the following compound.

Diethyl [N-cyclopropyl-N-[3-(4-methyl-1-piperazinyl)-2-ethyl-4-fluoro-6-nitrophenyl)aminomethylene]malonate

EXAMPLE 1

To 6,7-difluoro-1-cyclopropyl-8-methyl-1,4-dihydro-4-oxoquinoline-3-carboxylic acid-B(OCOCH$_3$)$_2$ chelate (1.2 g) are added 3-(N-benzyl-N-methylamino)-1-pyrrolidine (1.73 g) and dimethylacetamide (6 ml), and the mixture is reacted at 50° C. for 20 hours. After concentrating, the resulting residue is dissolved in acetone (20 ml) and thereto is added conc. hydrochloric acid (5 ml), and the mixture is stirred at room temperature for 30 minutes. After the solvent is distilled off, to the residue is added water, and the mixture is extracted with dichloromethane. The aqueous layer is taken and neutralized with aqueous sodium hydrogen carbonate, and is extracted with dichloromethane. The extracts are combined and dried over magnesium sulfate. After removing the solvent, the resulting residue is recrystallized from ethanol-diethyl ether to give 7-[3-(N-benzyl-N-methylamino)-1-pyrrolidinyl]-1-cyclopropyl-6-fluoro-8-methyl-1,4-dihydro-4-oxoquinoline-3-carboxylic acid (0.1 g), as pale yellow powder, m.p. 160.8°–161.3° C.

EXAMPLE 2

6,7-Difluoro-1-cyclopropyl-8-methyl-1,4-dihydro-4-oxoquinoline-3-carboxylic acid (1.8 g) is suspended in N-methylpyrrolidone (5 ml) and thereto is added 3-(N-benzyl-N-methylamino)-1-pyrrolidine (4.0 g), and the mixture is stirred at 150° C. for 3 hours. After the reaction, the reaction mixture is concentrated, and the resulting residue is recrystallized from ethanol-diethyl ether to give 7-[3-(N-benzyl-N-methylamino)-1-pyrrolidinyl]-1-cyclorpopyl-6-fluoro-8-methyl-1,4-dihydro-4-oxoquinoline-3-carboxylic acid (0.1 g), as pale yellow powder, m.p. 160.8°–161.3° C.

EXAMPLE 3

To ethyl 1-cyclopropyl-7-[3-(N-benzyl-N-methylamino)-1-pyrrolidinyl]-6-fluoro-8-methyl-1,4-dihydro-4-oxoquinoline-3-carboxylate (0.86 g) is added 10% aqueous sodium hydroxide (7 ml), and the mixture is refluxed for 5 hours. After cooling, the mixture is acidified with diluted hydrochloric acid and is extracted with dichloromethane. The aqueous layer is adjusted to about pH 7.5 with sodium hydrogen carbonate, and the resulting precipitates are recrystallized from ethanol-diethyl ether to give 7-[3-(N-benzyl-N-methylamino)-1-pyrrolidinyl]-1-cyclopropyl-6-fluoro-8-methyl-1,4-dihydro-4-oxoquinoline-3-carboxylic acid (0.32 g), as pale yellow powder, m.p. 160.8°–161.3° C.

EXAMPLE 4

In the same manner as described in Examples 1, 2 and 3 by using appropriate starting material, there are prepared the following compounds:

(1) 7-(3-Amino-1-pyrrolidinyl)-1-cyclopropyl-6-fluoro-8-methyl-1,4-dihydro-4-oxoquinoline-3-carboxylic acid, m.p. 201.5°–203.0° C., pale yellow powder (recrystallized from ethanol-diethyl ether)

(2) 1-Cyclopropyl-7-(4-hydroxy-1-piperidyl)-6-fluoro-8-methyl-1,4-dihydro-4-oxoquinoline-3-carboxylic acid, m.p. 234°–236° C. (recrystallized from chloroform-ethanol), pale yellow crystals.

(3) 1-Cyclopropyl-7-(3-amino-4-methyl-1-pyrrolidinyl)-6-fluoro-8-methyl-1,4-dihydro-4-oxoquinoline-3-carboxylic acid hydrochloride (isolmer A), m.p. 226°–232° C., yellow powder (recrystallized from ethyl acetate-ethanol).

NMR (DMSO-$d_6$) δ: 1.18 (3H, d, J=6.7 Hz), 2.62 (3H, s), 7.72 (1H, d, J=13.4 Hz), 8.79 (1H, s).

(4) 1-Cyclopropyl-7-(3-aminomethyl-1-pyrrolidinyl)-6-fluoro-8-methyl-1,4-dihydro-4-oxoquinoline-3-carboxylic acid hydrochloride, m.p. 195°–200° C. (recrystallized from ethyl acetate-methanol), yellow crystals.

(5) 1-Cyclopropyl-7-(3-methylamino-1-pyrrolidinyl)-6-fluoro-8-methyl-1,4-dihydro-4-oxoquinoline-3-carboxylic acid, m.p. 185.5°–187.5° C. (decomp.) (recrystallized from ethanol-diethyl ether), white powder.

(6) 1-Cyclopropyl-7-[3-(5-methyl-2-oxo-1,3-dioxolene-4-yl)methylamino-1-pyrrolidinyl]-6-fluoro-8-methyl-1,4-dihydro-4-oxoquinoline-3-carboxylic acid. (7) 1-Cyclopropyl-7-[3-(N-benzyl-N-methylamino)-1-pyrrolidinyl]-6-fluoro-8-methyl-1,4-dihydro-4-oxoquinoline-3-carboxylic acid, m.p. 160.8°–161.3° C. (recrystallized from ethanol-diethyl ether), pale yellow powder.

(8) 1-Cyclopropyl-7-(4-oxo-1-piperidyl)-6-fluoro-8-methyl-1,4-dihydro-4-oxoquinoline-3-carboxylic acid, m.p. 247°–250° C. (recrystallized from chloroform-ethanol), white crystals.

(9) 1-Cyclopropyl-7-(3-acetamidomethyl-1-pyrrolidinyl)-6-fluoro-8-methyl-1,4-dihydro-4-oxoquinoline-3-carboxylic acid, m.p., 192°–194° C. (recrystallized from chloroform-methanol), white crystals.

(10) 1-Cyclopropyl-7-(3-t-butoxycarbonylaminomethyl-1-pyrrolidinyl)-6-fluoro-8-methyl-1,4-dihydro-4-oxoquinoline-3-carboxylic acid, m.p. 131°–135° C. (recrystallized from methanol), white powder.

(11) 1-Cyclopropyl-7-(3-aminomethyl-1-pyrrolidinyl)-6-fluoro-8-methyl-1,4-dihydro-4-oxoquinoline-3-carboxylic acid hydrochloride, m.p. 195°–200° C. (recrystallized from ethyl acetate-methanol), white powder.

(12) 1-Cyclopropyl-7-[3-(N-ethylacetamido)methyl-1-pyrrolidinyl]-6-fluoro-8-methyl-1,4-dihydro-4-oxoquinoline-3-carboxylic acid, m.p. 167°–169° C. (recrystallized from ethanol), pale yellow crystals.

(13) 1-Cyclopropyl-7-(3-ethylaminomethyl-1-pyrrolidinyl)-6-fluoro-8-methyl-1,4-dihydro-4-oxoquinoline-3-carboxylic acid hydrochloride, m.p. 267°–271° C. (recrystallized from methanol-acetonitrile), yellow powder.

(14) 1-Cyclopropyl-7-(3,5-dimethyl-1-piperidyl)-6-fluoro-8-methyl-1,4-dihydro-4-oxoquinoline-3-carboxylic acid, m.p. 176°–179° C. (recrystallized from ethanol), pale yellow prisms.

(15) 1-Cyclopropyl-7-(4-fluoro-1-piperidinyl)-6-fluoro-8-methyl-1,4-dihydro-4-oxoquinoline-3-carboxylic acid, m.p. 208°–210° C. (recrystallized from ethanol), colorless needles.

(16) 1-Cyclopropyl-7-[3-(5-methyl-2-oxo-1,3-dioxolen-4-yl)methylamino-1-pyrrolidinyl]-6-fluoro-8-methyl-1,4-dihydro-4-oxoquinoline-3-carboxylic acid.

(17) 1-Cyclopropyl-7-(3-amino-1-pyrrolidinyl)-6-fluoro-8-ethyl-1,4-dihydro-4-oxoquinoline-3-carboxylic acid.

(18) 1-Cyclopropyl-7-(3-amino-4-methyl-1-pyrrolidinyl)-6-fluoro-8-ethyl-1,4-dihydro-4-oxoquinoline-3-carboxylic acid.

(19) 1-Cyclopropyl-7-(3-amino-4-methyl-1-pyrrolidinyl)-6-fluoro-8-methyl-1,4-dihydro-4-oxoquinoline-3-carboxylic acid hydrochloride (isomer B), m.p. 209°–213° C. (recrystallized from ethyl acetate-ethanol), yellow powder.

NMR (DMSO-$d_6$) δ: 1.15 (3H, d, J=6.9 Hz), 2.76 (3H, s), 7.70 (1H, d, J=13.7 Hz), 8.77 (1H, s).

(20) 1-Cyclopropyl-7-(3-t-butoxycarbonylamino-4-methyl-1-pyrrolidinyl)-6-fluoro-8-methyl-1,4-dihydro-4-oxoquinoline-3-carboxylic acid (isomer A), m.p. 157°–160° C. recrystallized from ethyl acetate), yellow crystal.

NMR (CDCl$_3$) δ: 1.20 (3H, d, J=6.6 Hz), 2.57 (3H, s), 7.91 (1H, d, J=13.3 Hz), 9.15 (1H, s).

(21) 1-Cyclopropyl-7-(3-t-butoxycarbonylamino-4-methyl-1-pyrrolidinyl)-6-fluoro-8-methyl-1,4-dihydro-4-oxoquinoline-3-carboxylic acid (isomer B), m.p. 199°–202° C. (recrystallized from ethyl acetate), yellow powder.

NMR (CDCl$_3$) δ: 1.12 (3H, d, J=6.6 Hz), 2.58 (3H, s), 7.85 (1H, d, J=13.6 Hz), 8.87 (1H, s).

(22) 1-Cyclopropyl-7-(3-t-butoxycarbonylamino-1-pyrrolidinyl)-6-fluoro-8-methyl-1,4-dihydro-4-oxoquinoline-3-carboxylic acid, m.p. 117°–120° C. (recrystallized from ethanol), pale yellow prisms.

EXAMPLE 5

1-Cyclopropyl-7-(4-oxo-1-piperidyl)-6-fluoro-8-methyl-1,4-dihydro-4-oxoquinoline-3-carboxylic acid (0.25 g) is dissolved in 1% aqueous sodium hydroxide (28 ml), and thereto is added sodium boron hydroxide (0.1 g) at room temperature. The mixture is stirred at the same temperature for 30 minutes, and the resulting mixture is poured into ice water and then acidified with conc. sulfuric acid. The mixture is extracted with dichloromethane, and the solvent is distilled off. The resulting residue is crystallized by adding thereto ethyl acetate, and then recrystallized from chloroform-methanol to give 1-cyclopropyl-7-(4-hydroxy-1-piperidyl)-6-fluoro-8-methyl-1,4dihydro-4-oxoquinoline-3-carboxylic acid (0.16 g), as pale yellow crystals, m.p. 234°-236° C.

EXAMPLE 6

To 1-cyclopropyl-7-[3-(t-butoxycarbonylaminomethyl)-1-pyrrolidinyl]-6-fluoro-8-methyl-1,4-dihydro-4-oxoquinoline-3-carboxylic acid (0.1 g) are added 10% hydrochloric acid (4 ml) and ethanol (2 ml), and the mixture is reacted at 70° C. for 10 minutes. After concentrating, the resulting residue is crystallized by adding thereto diethyl ether and then recrystallized from ethyl acetate-methanol to give 1-cyclopropyl-7-(3-aminomethyl-1-pyrrolidinyl)-6-fluoro-8-methyl-1,4-dihydro-4-oxoquinoline-3-carboxylic acid hydrochloride (45 mg), as yellow crystals, m.p. 195°-200° C.

EXAMPLE 7

To 1-cyclopropyl-7-[3-(N-ethylacetamido)methyl-1-pyrrolidinyl]-6-fluoro-8-methyl-1,4-dihydro-4-oxoquinoline-3-carboxylic acid hydrochloride (0.22 g) is added 5% aqueous sodium hydroxide (10 ml), and the mixture is refluxed for 24 hours. After cooling, the insoluble materials are filtered off, and the filtrate is acidified with conc. hydrochloric acid. The mixture is extracted with dichloromethane, and the aqueous layer is made alkaline with aqueous sodium hydroxide, and thereto is added t-butoxycarboxylic anhydride (200 mg). The mixture is stirred at room temperature for 30 minutes. The reaction mixture is acidified with 10% hydrochloric acid and is extracted with dichloromethane. After removing the solvent by concentration, to the resulting residue are added 10% hydrochloric acid (5 ml) and methanol (10 ml), and the mixture is heated at 70° C. for 30 minutes. After concentrating, the resulting residue is recrystallized from methanol-acetonitrile to give 1-cyclopropyl-7-(3-ethylaminomethyl-1-pyrrolidinyl)-6-fluoro-8-methyl-1,4-dihydro-4-oxoquinoline-3-carboxylic acid hydrochloride (30 mg), as yellow crystals, m.p. 267°-271° C.

EXAMPLE 8

To 1-cyclopropyl-7-(3-amino-1-pyrrolidinyl)-6-fluoro-8-methyl-1,4-dihydro-4-oxoquinoline-3-carboxylic acid (0.38 g) are added formic acid (3 ml), 37% formalin (3 ml) and sodium formate (0.4 g), and the mixture is refluxed for 5 hours. After cooling, the reaction mixture is poured into ice water and adjusted to below pH 8 with aqueous sodium hydrogen carbonate, and the mixture is extracted with dichloromethane. After removing the solvent by concentration, the resulting residue is recrystallized from ethanol-diethyl ether to give 1-cyclopropyl-7-(3-methylamino-1-pyrrolidinyl)-6-fluoro-8-methyl-1,4-dihydro-4-oxoquinoline-3-carboxylic acid (0.1 g), as white powder, m.p. 185.5°-187.5° C. (decomp.)

In the same manner as described above using appropriate starting materials, there are prepared the same compounds as 1st compound in 7th and 13th in Example 4.

EXPERIMENT (Antimicrobial Activity in In Vitro)

The antimicrobial activity of the test compounds as mentioned below was tested by measuring minimum inhibitory concentration (MIC) by the serial dilution method on agar plate [cf. Chemotherapy, 22, 1126–1128 (1974)]. The microorganisms were used in a concentration of $1 \times 10^8$ cells/ml (O.D. 660 mµ, 0.07–0.16) and $1 \times 10^6$ cells/ml (100 folds dilution). When *S. penumoniae* type II and *S. pneumoniae* type III were used as the test microorganism, the medium contained 5% horse blood. The results are shown in Table 1.

[Test Compound]

1. 7-(3-Amino-1-pyrrolidinyl)-1-cyclopropyl-6-fluoro-8-methyl-1,4-dihydro-4-oxoquinoline-3-carboxylic acid
2. 1-Cyclopropyl-7-(3-acetamidomethyl-1-pyrrolidinyl)-6-fluoro-8-methyl-1,4-dihydro-4-oxoquinoline-3-carboxylic acid.
3. 1-Cyclopropyl-7-(4-oxo-1-piperidinyl)-6-fluoro-8-methyl-1,4-dihydro-4-oxoquinoline-3-carboxylic acid
4. 1-Cyclopropyl--(4-hydroxy-1-piperidinyl)-6-fluoro-8-methyl-1,4-dihydro-4-oxquinoline-3l -carboxylic acid
5. 1-Cyclopropyl-7-[3-(t-butoxycarbonylaminomethyl)-1-pyrrolidinyl]-6-fluoro-8-methyl-1,4-dihydro-4-oxoquinoline-3-carboxylic acid
6. 1-Cyclopropyl-7-(3-aminomethyl-1-pyrrolidinyl)-6-fluoro-8-methyl-1,4-dihydro-4-oxoquinoline-3-carboxylic acid
7. 1-Cyclopropyl-7-[3-(N-methyl-N-benzylamino)-1-pyrrolidinyl]-6-fluoro-8-methyl-1,4-dihydro-4-oxoquinoline-3-carboxylic acid
8. 1-Cyclopropyl-7-(3-methylamino-1-pyrrolidinyl)-6-fluoro-8-methyl-1,4-dihydro-4-oxoquinoline-3-carboxylic acid
9. 1-Cyclopropyl-7-(3-ethylaminomethyl-1-pyrrolidinyl)-6-fluoro-8-methyl-1,4dihydro-4-oxoquinoline-3-carboxylic acid
10. 1-Cyclopropyl-7-(3-amino-4-methyl-1-pyrrolidinyl)-6-fluoro-8-methyl-1,4-dihydro-4oxoquinoline-3-carboxylic acid hydrochloride (isomer A)
11. 1-Cyclopropyl-7-(3,5-dimethyl-1-piperidinyl)-6-fluoro-8-methyl-1,4-dihydro-4-oxoquinoline-3-carboxylic acid
12. 1-Cyclopropyl-7-(4-fluoro-1-piperidinyl)-6-fluoro-8-methyl-1,4-dihydro-4-oxoquinoline-3-carboxylic acid

[Test Microorganisms]

A: *Staphylococcus aureus* FDS 209A
B: *Staphylococcus pyrogens* IID S-23
C: *Staphylococcus pneumoniae* type II
D: *Staphylococcus pneumoniae* type III
E: *Pseudomonas aeruginosa* E-2
F: *Bacteroides fragilis* GM7000
G: *Eubacterium limosum* ATCC 8496
H: *Peptococcus anaerobis* GM1003
I: *Propionibacterium acnes* ATCC 6919
J: *Propionibacterium granulosum* ATCC 25564
K: *Enterococcus faecalis*

TABLE 1

| Test micro-organisms | Test Compd. No. 1 $1 \times 10^6$ cells/ml | Test Compd. No. 2 $1 \times 10^6$ cells/ml | Test Compd. No. 3 $1 \times 10^6$ cells/ml | Test Compd. No. 4 $1 \times 10^6$ cell/ml |
|---|---|---|---|---|
| A | 0.048 | 0.024 | <0.006 | 0.012 |
| B | 0.048 | 0.024 | 0.097 | 0.048 |
| C | — | — | — | — |
| D | — | — | — | — |
| E | 0.195 | — | 1.56 | 0.78 |
| F | — | — | — | — |
| G | — | — | — | — |
| H | — | — | — | — |
| I | — | — | — | — |
| J | — | — | — | — |

TABLE 1-continued

| Test micro-organisms | Test Compd. No. 5 $1 \times 10^6$ cells/ml | Test Compd. No. 6 $1 \times 10^6$ cells/ml | Test Compd. No. 7 $1 \times 10^6$ cells/ml | Test Compd. No. 8 $1 \times 10^6$ cell/ml |
|---|---|---|---|---|
| A | 0.048 | <0.006 | 0.048 | 0.024 |
| B | 0.195 | <0.006 | 0.195 | 0.048 |
| C | — | — | — | — |
| D | — | — | — | — |
| E | — | 0.39 | — | 0.39 |
| F | — | — | — | — |
| G | — | — | — | — |
| H | — | — | — | — |
| I | — | — | — | — |
| J | — | — | — | — |
| K | — | — | — | — |

| Test micro-organisms | Test Compd. No. 9 $1 \times 10^6$ cells/ml | Test Compd. No. 10 $1 \times 10^6$ cells/ml | Test Compd. No. 11 $1 \times 10^6$ cells/ml | Test Compd. No. 12 $1 \times 10^6$ cell/ml |
|---|---|---|---|---|
| A | <0.006 | 0.024 | 0.097 | 0.012 |
| B | 0.012 | 0.024 | — | — |
| C | — | — | — | — |
| D | — | — | — | — |
| E | 0.78 | 0.195 | — | 0.78 |
| F | — | — | — | — |
| G | — | — | — | — |
| H | — | — | — | — |
| I | — | — | — | — |
| J | — | — | — | — |
| K | — | — | — | — |

What is claimed is:

1. A compound of the formula:

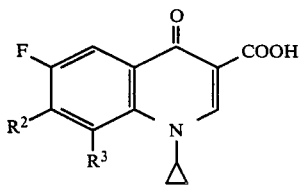

wherein $R^2$ is a 1-pyrrolidinyl group of the formula:

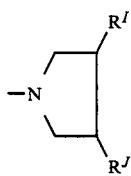

wherein $R^I$ is an amino-($C_1$-$C_6$) alkyl group, said amino group may be substituted by one $C_1$-$C_6$ alkyl group, or an amino group which may be substituted by one $C_1$-$C_6$ alkyl group; and $R^J$ is hydrogen atom or a $C_1$-$C_6$ alkyl group or a 1-piperidinyl group which may have one substituent selected from the group consisting of oxo, hydroxy, and halogen, and $R^3$ is methyl, or a pharmaceutically acceptable salt thereof.

2. The compound according to claim 1, wherein $R^I$ is an amino group which may be substituted by one $C_1$-$C_6$ alkyl group, and $R^J$ is hydrogen atom.

3. The compound according to claim 1, wherein $R^I$ is an amino-($C_1$-$C_6$)alkyl group, said amino group being substituted by one $C_1$-$C_6$ alkyl group, and $R^J$ is hydrogen atom.

4. The compound according to claim 1, wherein $R^I$ is an amino group, and $R^J$ is a $C_1$-$C_6$ alkyl group.

5. The compound according to claim 1, wherein $R^I$ is an amino group, and $R^J$ is hydrogen atom.

6. The compound according to claim 1, wherein $R^2$ is a 1-piperidinyl group which may have a substituent selected from the group consisting of oxy, hydroxy and a halogen atom.

7. A compound of the formula:

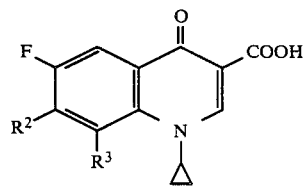

wherein $R^2$ has the formula

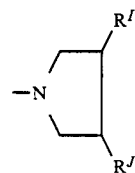

wherein $R^I$ is an amino-($C_1$-$C_6$) alkyl group, said amino group may be substituted by one $C_1$-$C_6$ alkyl group, or an amino group which may be substituted by one $C_1$-$C_6$ alkyl group; and $R^J$ is hydrogen atom or a $C_1$-$C_6$ alkyl group; or a 1-piperidinyl group which may have one substituent selected from the group consisting of oxo, hydroxy, and halogen, provided that when $R^I$ is amino, $R^J$ is not a hydrogen atom, and $R^3$ is methyl, or a pharmaceutically acceptable salt thereof.

8. The compound according to claim 7, wherein $R^I$ is an amino group which is substituted by one $C_1$-$C_6$ alkyl group and $R^J$ is hydrogen atom.

9. The compound according to claim 7, wherein $R^I$ is an amino-($C_1$-$C_6$)alkyl group, said amino group being substituted by one $C_1$-$C_6$ alkyl group, and $R^J$ is hydrogen atom.

10. The compound according to claim 7, wherein $R^I$ is an amino group, and $R^J$ is a $C_1$-$C_6$ alkyl group.

11. The compound according to claim 7, wherein $R^2$ is a 1-piperidinyl group which may have a substituent selected from the group consisting of oxo, hydroxy and a halogen atom.

12. A compound of the formula:

wherein $R^2$ is a 1-pyrrolidinyl group which is substituted by 1 to 3 substituents selected from the group consisting of (i) a $C_1$-$C_6$ alkyl group, (ii) an amino-($C_1$-$C_6$) alkyl group, said amino group may be substituted by one or two $C_1$-$C_6$ alkyl groups, and (iii) an amino group which may be substituted by one or two $C_1$-$C_6$ alkyl groups, and $R^3$ is a $C_1$-$C_6$ alkyl group, or a pharmaceutically acceptable salt thereof.

13. The compound according to claim 12, wherein $R^2$ is a 1-pyrrolidinyl group of the formula:

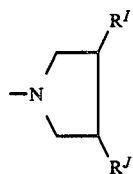

wherein $R^I$ is an amino-($C_1$-$C_6$)alkyl group, said amino group may be substituted by 1 or 2 $C_1$-$C_6$ aklyl groups, or an amino group which may be substituted by 1 or 2 $C_1$-$C_6$ alkyl groups; and $R^J$ is hydrogen atom or a $C_1$-$C_6$ alkyl group.

14. The compound according to claim 13, wherein $R^I$ is an amino group which may be substituted by one $C_1$-$C_6$ alkyl group.

15. The compound according to claim 13, where $R^I$ is an amino-($C_1$-$C_6$)alkyl group, said amino group being substituted by one $C_1$-$C_6$ alkyl group, and $R^J$ is hydrogen atom.

16. The compound according to claim 14, wherein $R^3$ is methyl.

17. The compound according to claim 15, wherein $R^3$ is methyl.

18. A compound of the formula:

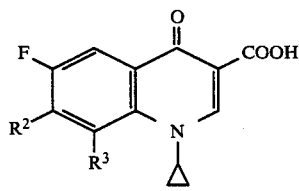

wherein $R^2$ is a 1-piperidinyl group which may have 1 to 3 substituents selected from the group consisting of oxo, hydroxy, a halogen and a $C_1$-$C_6$ alkyl, and $R^3$ is a $C_1$-$C_6$ alkyl group, or a pharmaceutically acceptable salt thereof.

19. The compound according to claim 18, wherein $R^2$ is a 1-piperidinyl group which is substituted by one halogen atom.

20. The compound according to claim 19, wherein $R^3$ is methyl.

21. The compound according to claim 18, wherein $R^2$ is a 1-piperidinyl group which is substituted by one substituent selected from hydroxy and oxo groups.

22. 1-Cyclopropyl-7-(4-fluoro-1-piperidinyl)-6-fluoro-8-methyl-1,4-dihydro-4-oxoquinoline-3-carboxylic acid.

23. 7-(3-Amino-1-pyrrolidinyl)-1-cyclopropyl-6-fluoro-8-methyl-1,4-dihydro-4-oxoquinoline-3-carboxylic acid.

24. 1-Cyclopropyl-7-(3-aminomethyl-1-pyrrolidinyl)-6-fluoro-8-methyl-1,4-dihydro-4-oxoquinoline-3-carboxylic acid.

25. 1-Cyclopropyl-7-(3-methylamino-1-pyrrolidinyl)-6-fluoro-8-methyl-1,4-dihydro-4-oxoquinoline-3-carboxylic acid.

26. 1-Cyclopropyl-7-(3-ethylaminomethyl-1-pyrrolidinyl)-6-fluoro-8-methyl-1,4-dihydro-4-oxoquinoline-3-carboxylic acid.

27. 1-Cyclopropyl-7-(3-amino-4-methyl-1-pyrrolidinyl)-6-fluoro-8-methyl-1,4-dihydro-4-oxoquinoline-3-carboxylic acid.

28. An antimicrobial composition which comprises as an esstential active ingredient an effective antimicrobial amount of a compound as defined in claim 1 in admixture with a pharmaceutically acceptable diluent or carrier.

29. An antimicrobial composition which comprises as an essential active ingredient an effective antimicrobial amount of the compound defined in claim 7 in admixture with a pharmaceutically acceptable diluent or carrier.

30. An antimicrobial composition which comprises as an essential active ingredient an effective antimicrobial amount of a compound selected from the group consisting of 7-(3-amino-1-pyrrolidinyl)-1-cyclopropyl-6-fluoro-8-methyl-1,4-dihydro-4-oxoquinoline-3-carboxylic acid, 1-cyclopropyl-7-(3-aminomethyl-1-pyrrolidinyl)-6-fluoro-8-methyl-1,4-dihydro-4-oxoquinoline-3-carboxylic acid, 1-cyclopropyl-7-(3-methylamino-1-pyrrolidinyl)-6-fluoro-8-methyl-1,4-dihydro-4-oxoquinoline-3-carboxylic acid, 1-cyclopropyl-7-(3-ethylaminomethyl-1-pyrrolidinyl-6-fluoro-8-methyl-1,4-dihydro-4-oxoquinoline-3-carboxylic acid, 1-cyclopropyl-7-(3-amino-4-methyl-1-pyrrolidinyl)-6-fluoro-8-methyl-1,4-dihydro-4-oxoquinoline-3-carboxylic acid, and 1-cyclopropyl-7-(4-fluoro-1-piperidinyl)-6-fluoro-8-methyl-1,4-dihydro-4-oxoquinoline-3-carboxylic acid in admixture with a pharmaceutically acceptable diluent or carrier.

* * * * *